United States Patent
Siekmann et al.

(10) Patent No.: US 9,566,311 B2
(45) Date of Patent: Feb. 14, 2017

(54) PHARMACEUTICAL COMPOSITION

(75) Inventors: Britta Siekmann, Lomma (SE);
Mattias Malm, Copenhagen (DK);
Anders Nilsson, Copenhagen (DK);
Kazimierz Wisniewski, Copenhagen (DK)

(73) Assignee: Ferring B.V., Hoofddorp (NL)

( * ) Notice: Subject to any disclaimer, the term of this patent is extended or adjusted under 35 U.S.C. 154(b) by 0 days.

(21) Appl. No.: 13/824,132

(22) PCT Filed: Sep. 29, 2011

(86) PCT No.: PCT/IB2011/002394
§ 371 (c)(1),
(2), (4) Date: May 3, 2013

(87) PCT Pub. No.: WO2012/042371
PCT Pub. Date: Apr. 5, 2012

(65) Prior Publication Data
US 2013/0210746 A1    Aug. 15, 2013

(30) Foreign Application Priority Data
Sep. 30, 2010 (EP) ..................... 10251690

(51) Int. Cl.
| | | |
|---|---|---|
| *A61K 38/12* | (2006.01) | |
| *A61K 9/00* | (2006.01) | |
| *A61K 38/11* | (2006.01) | |
| *A61K 47/12* | (2006.01) | |
| *A61K 47/18* | (2006.01) | |

(52) U.S. Cl.
CPC ............ *A61K 38/12* (2013.01); *A61K 9/0019* (2013.01); *A61K 9/0043* (2013.01); *A61K 38/11* (2013.01); *A61K 47/12* (2013.01); *A61K 47/183* (2013.01)

(58) Field of Classification Search
CPC .... A61K 9/0019; A61K 9/0043; A61K 38/11; A61K 47/12; A61K 47/183; A61K 38/12
See application file for complete search history.

(56) References Cited

U.S. PATENT DOCUMENTS

| | | | |
|---|---|---|---|
| 7,635,473 B2 * | 12/2009 | Warne et al. ............. | 424/133.1 |
| 2001/0027177 A1 | 10/2001 | Woodrow | |
| 2003/0119728 A1 | 6/2003 | Scheidl et al. | |
| 2003/0138417 A1 | 7/2003 | Kaisheva et al. | |
| 2004/0235956 A1 * | 11/2004 | Quay ........................... | 514/573 |

FOREIGN PATENT DOCUMENTS

| | | | |
|---|---|---|---|
| EP | 0916347 A1 | 5/1999 | |
| EP | 2174652 A2 | 4/2010 | |
| WO | WO9501185 * | 1/1995 | ............. A61K 38/11 |
| WO | WO9501185 A1 | 1/1995 | |
| WO | 2004062689 A1 | 7/2004 | |
| WO | WO2008042452 A1 | 4/2008 | |
| WO | WO 2008150305 A1 * | 12/2008 | ............. A61K 9/08 |
| WO | WO2008150305 A1 | 12/2008 | |
| WO | WO2009122285 * | 10/2009 | ............. C07K 7/16 |
| WO | WO2009122285 A8 | 12/2009 | |

OTHER PUBLICATIONS

Remington: The Science and Practice of Pharmacy, Alfonso R. Gennaro, Ed., 20th Edition, 2000, (only pp. 245, 1690 provided herewith).*
Product Monograph Duratocin, Ferring Inc. Mar. 29, 2006 revision.*
Hawe et al., Towards Heat-stable Oxytocin Formulations: Analysis of Degradation Kinetics and Identification of Degradation Products, Pharm. Res, vol. 26, No. 7, Jul. 2009.*
Rath et al.; "Prevention of postpartum haemorrhage with the oxytocin analogue carbetocin"; European Journal of Obstetrics & Gynecology and Reproductive Biology; vol. 147; No. 1; pp. 15-20 (2009).
International Search Report mailed Feb. 1, 2013, which issued in corresponding International Application No. PCT/IB2011/002394.
Office Action issued on May 26, 2015 in corresponding Japanese Application No. 2013-530810, and English translation thereof, 6 pages.

* cited by examiner

*Primary Examiner* — Lianko Garyu
*Assistant Examiner* — Joseph Fischer
(74) *Attorney, Agent, or Firm* — Fish & Richardson P.C.

(57) ABSTRACT

The present invention relates to pharmaceutical compositions having improved stability.

17 Claims, 8 Drawing Sheets

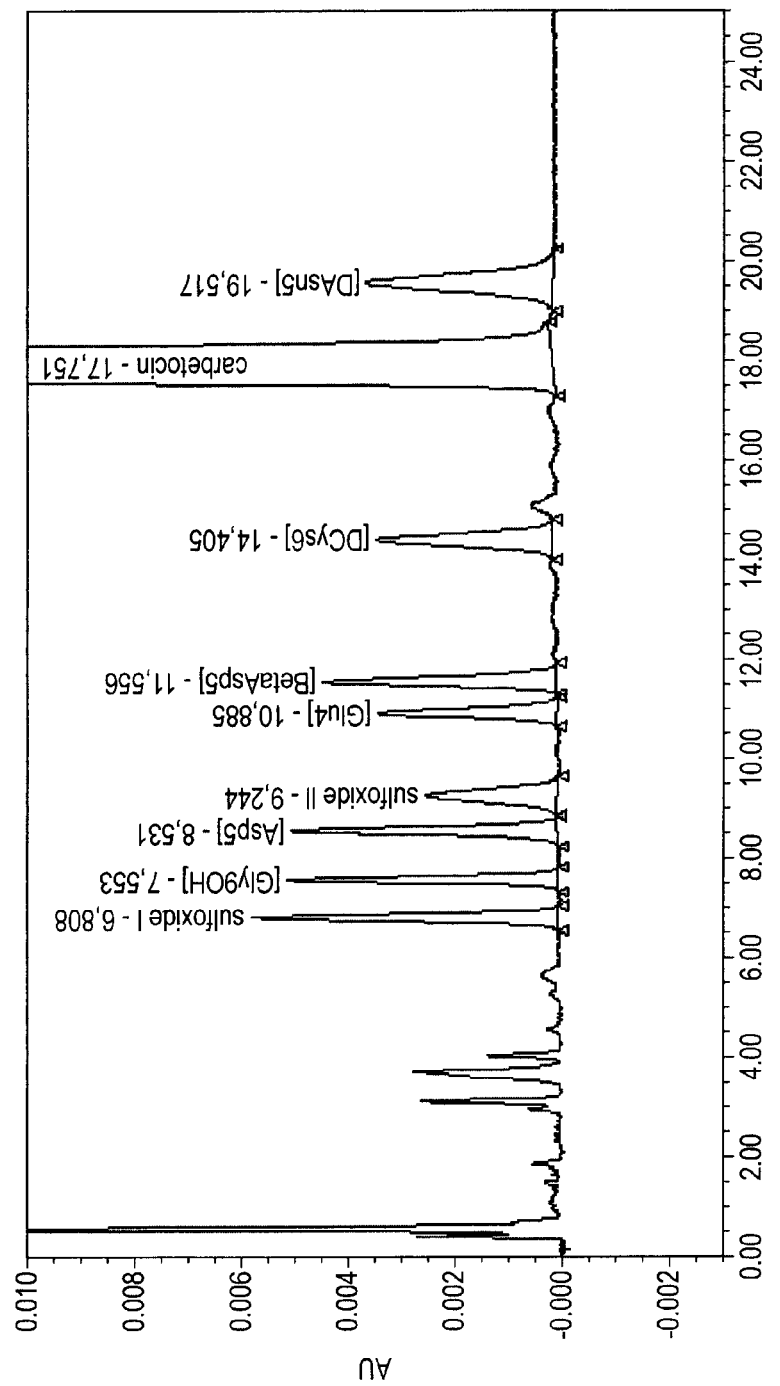

Carbetocin:

[Gly9OH]carbetocin:

[Glu4]carbetocin:

[Asp5]carbetocin:

[betaAsp5]carbetocin:

[DAsn5]carbetocin:

sulfoxide I+II carbetocin (two structural isomers)

sulfoxide I has the R-configuration on the sulphur atom, sulfoxide II has the S-configuration).

individual degradation products at different pH (pH study, constant antioxidant)

shows the sum of degradation products at different pH (pH study, constant antioxidant)

PHARMACEUTICAL COMPOSITION

CROSS REFERENCE TO PRIOR APPLICATIONS

This is a U.S. National Phase application under 35 U.S.C. §371 of International Patent Application No. PCT/IB2011/002394, filed Sep. 29, 2011 and claims the priority of European Patent Application No. 10251690.3, filed Sep. 30, 2010 both of which are incorporated by reference herein in their entirety. The International Application published in English on Apr. 5, 2012 as WO 2012/042371 under PCT Article 21(2).

The present invention relates to pharmaceutical compositions, for example pharmaceutical compositions for the treatment of post-partum haemorrhage (PPH) or other medical applications. In particular, it relates to pharmaceutical compositions having improved stability, for example at room or ambient temperature.

Postpartum haemorrhage (PPH) is one of the leading causes of pregnancy-related mortality and severe morbidity in developing countries as well as in the industrialised world. It is a potentially life-threatening condition which is demonstrated by about 140,000 deaths annually, one every four minutes, the vast majority among women who do not have access to adequate obstetric healthcare. Although the problem is numerically important, not all regions of the industrialised world are similarly affected and in Europe, the rates of death associated with maternal haemorrhage vary widely from one country to another. A population based survey in 11 regions within European countries showed that rates of severe haemorrhage ranged from 0.1% to 0.9% of pregnancies (MOMS-B group, 1999). There are good reasons to believe that differences in clinical practice may be of great importance to the differences in morbidity/mortality. In the United Kingdom, the Confidential Enquiry into Maternal Deaths, covering the years 1994-1996, showed that after action had been taken in all maternity units to establish guidelines for management of third stage and postpartum haemorrhage, there were no deaths from haemorrhage in uncomplicated vaginal births (Department of Health et al, 1998). This achievement supports the assumption that clinical management has a key role in prevention of severe maternal haemorrhage.

PPH is difficult to manage because evaluation of blood loss in the delivery unit is unreliable. Action is often taken in response to the development of maternal signs such as hypotension or malaise rather than on the basis of estimated blood loss. The delayed action is responsible for many cases of severe haemorrhage, and immediate surgery may be required because time spent using other treatment methods would be dangerous for the patient. These considerations speak in favour of the application of a policy of routine prophylactic administration of a uterotonic to all parturients. The case for such a policy is augmented by the fact that uterine atony is the most significant contributor to PPH. Uterine atony is a loss of tone in the uterine musculature. Normally, contraction of the uterine muscle compresses the vessels and reduces flow. This increases the likelihood of coagulation and prevents bleeds. Thus, lack of uterine muscle contraction can cause an acute haemorrhage. Clinically, 75-80% of postpartum hemorrhages are due to uterine atony.

Reviews have shown compelling evidence in support of routine prophylactic administration of a uterotonic, either in isolation or as part of the entity Active Management of the Third Stage of Labour (AMTSL); AMTSL is usually defined as an intervention with three components: a prophylactic administration of a uterotonic agent, early cord clamping and controlled cord traction. Further, AMTSL is shown to be equally effective in "low-risk" and "high-risk" women. Today, the use of a uterotonic drug as prophylaxis in all vaginal hospital deliveries to prevent severe haemorrhage is routine clinical management in most of Europe, and the practice is increasing globally.

The uterotonic drugs currently available are oxytocin, ergometrine, Syntometrine® (a combination of oxytocin and ergometrine) and misoprostol. However, these are not without disadvantages. Misoprostol is administered orally or vaginally and is less efficacious than injectable uterotonics; it is generally recommended that it is not used where injectable uterotonics are available. Syntometrine® is licensed in only a few countries in Europe. It is possibly more effective than oxytocin alone but is associated with more side effects, particularly nausea and vomiting. Further, it is unsuitable for use in women with hypertension, preeclampsia and heart disease, thereby reducing its suitability for routine prophylactic usage. Oxytocin itself has the disadvantage of a short half-life. Although this can be circumvented by administration as a continuous intravenous infusion to provide sustained uterotonic activity, this is more inconvenient than a single injection. If administered as a single bolus dose, whether as intravenous or intramuscular injection, close monitoring of uterine tone is required and additional uterotonic medication may be required due to the short half-life.

Carbetocin [(1-desamino-1-monocarba-2(O-methyl)-tyrosine)oxytocin] is a long-acting synthetic analogue of oxytocin, with agonist action. Carbetocin (PABAL®, DURATOCIN®) is currently approved for the prevention of uterine atony following delivery of the infant by Caesarean section under epidural or spinal anaesthesia. In its present marketed usage, intravenous administration of carbetocin provides a half-life of approximately 40 minutes, which is 4 to 10 times longer than the reported half-life of oxytocin (4 to 10 minutes). However, using intramuscular injection, carbetocin reaches peak plasma concentrations in less than thirty minutes and has a bioavailability of 80% (W Rath, European Journal of Obstetrics and Gynaecology and Reproductive Biology 147 (2009) 15-20). Thus, carbetocin has the potential to be a near ideal drug for routine postpartum haemorrhage prophylaxis, offered in all hospital vaginal deliveries, because it is suitable for both intramuscular injection and intravenous administration, offering convenience and simple implementation; it has quick onset of action; is long-acting, especially compared to oxytocin; is rarely associated with adverse drug reactions; and has excellent tolerability. In published clinical trials, carbetocin has shown efficacy similar to oxytocin and Syntometrine® or even a trend towards better efficacy, demonstrated on several outcomes: blood loss (measured or estimated), incidence of blood loss >500 ml, additional use of uterotonic medication or total uterotonic interventions. Thus, carbetocin should offer an improvement over currently available options for prevention of uterine atony and excessive bleeding following vaginal delivery. In comparison with oxytocin, its advantage is primarily that it would replace the need for continuous infusion or additional uterotonic intervention. In practice, carbetocin has the potential to replace 2-4 hours of postpartum routine infusion therapy, and/or to improve outcome versus oxytocin bolus injection. Further, any reduction in additional interventions represents a favourable pharmacoeconomic case for use of carcetocin. In comparison with Syntometrine®, its advantage is primarily better tolerability and safety and lack of important contraindications. In either case, carbetocin is better suited for, and is likely to facilitate the implementation of, routine prophylactic usage.

The current carbetocin formulation (PABAL® 100 micrograms/mL solution for injection, Ferring Pharmaceuticals Limited) is not room temperature (RT) stable and requires refrigerated storage at a temperature of 2-8° C. There is, therefore, a need for a formulation of carbetocin which is room temperature stable (for example at 25° C. and 60% relative humidity) for up to two years, allowing, for example, use in ambulances. This would provide an advantage in climatic zone I/II. More importantly, there is a need for a formulation which may be stored unrefrigerated in climatic zone III/IV (high temperature, e.g. tropical) regions—that is meeting the temperature and humidity stability requirements for these zones, for example, a documented long-term temperature stability at 30° C. and relative humidity up to 75%. The climatic zone terminology is used by the FDA and EMEA and is familiar to those skilled in the art. Thus, climatic zone I is a temperate climate; climatic zone II is a subtropical and mediterranean climate; climatic zone III is hot and dry; and climatic zone IV is hot and humid.

According to the present invention there is provided a liquid composition (e.g. a liquid pharmaceutical composition) comprising carbetocin or a pharmaceutically active salt thereof; wherein the pH of the composition is from 5.0 to 6.0. The pH of the composition may be from 5.1 to 6.0, for example from 5.2 to 6, for example from 5.26 to 6. The pH of the composition may be from 5.15 to 5.75, for example from 5.2 to 5.65. The pH of the composition may be from 5.26 to 5.8, for example from 5.26 to 5.75, for example from 5.26 to 5.7, for example from 5.26 to 5.65, for example 5.4 to 5.65. Preferably, the liquid composition (e.g. a liquid pharmaceutical composition) comprises carbetocin.

Preferably the composition is an aqueous composition (e.g. an aqueous pharmaceutical composition) comprising carbetocin or a pharmaceutically active salt thereof; wherein the pH of the composition is from 5.0 to 6.0. The pH of the composition may be from 5.1 to 6.0, for example from 5.2 to 6, for example from 5.26 to 6. The pH of the composition may be from 5.15 to 5.75, for example from 5.2 to 5.65. The pH of the composition may be from 5.26 to 5.8, for example from 5.26 to 5.75, for example from 5.26 to 5.7, for example from 5.26 to 5.65, for example 5.4 to 5.65. It will be appreciated that the composition of the invention is preferably an aqueous solution. Although water (e.g. water for injection or WFI) is the preferred solvent, other solvents (mixtures of water with other pharmaceutically acceptable solvents, pharmaceutically acceptable alcohols, etc.) may be used.

The Applicants have found (Examples 1 to 3) that a composition, e.g. a pharmaceutical composition, comprising carbetocin or pharmaceutically active salt thereof, and having pH within a defined specific pH range, may be stored at room temperature (e.g. at 25° C. and 60% relative humidity) for a sustained period (e.g. up to 2 years). The composition may also have a long-term temperature stability at 30° C. and 40° C. and relative humidity up to 75%, and therefore be suitable for use in zone III/IV regions without requirement for refrigeration.

The composition may include (comprise) a buffering agent, for example a pharmaceutically acceptable buffering agent. Herein, the term buffering agent is an agent which is capable of driving an acidic or basic solution to a certain pH state, and then preventing a change from that state; in other words a buffering agent is an agent which is added to an already acidic or basic solution to modify the pH and then maintain the pH at the modified level. Generally a buffering agent is a weak acid or a weak base that would be comprised in a buffer solution, and be responsible for the buffering action seen in these solutions. The buffering agent may be, for example, acetic acid, adipic acid, citric acid, maleic acid, succinic acid or phosphate (e.g. sodium phosphate, e.g. sodium phosphate dibasic dihydrate). Preferably, the buffering agent is succinic acid. The composition may include a single buffering agent (i.e. not include two or more buffering agents). The composition may include two or more buffering agents (e.g. citric acid and (e.g. sodium) phosphate.

In another aspect, the composition may include (comprise) a buffer solution. Herein, the term buffer or buffer solution means a solution including a mixture of a weak acid and its conjugate base or a weak base an its conjugate acid, which has the property that the pH of the solution changes very little when a small amount of strong acid or base is added, such that the pH of the buffer (solution) is maintained. The buffer (solution) may be, for example, a citrate buffer (solution), comprising citric acid and a citrate (e.g. sodium citrate); a succinate buffer (solution) comprising succinic acid and a succinate (e.g. sodium succinate), an acetate buffer (solution) comprising acetic acid and an acetate (e.g. sodium acetate); a citrate/phosphate buffer (solution) comprising citric acid and phosphate; or a phosphate buffer (solution) comprising e.g. (monosodium) phosphate and its conjugate base, (disodium phosphate). A preferred buffer is a succinate buffer. The composition may include a single buffer (i.e. not include two or more buffers). The composition may include two or more buffers.

The Applicants have found that inclusion of succinic acid buffering agent (or use of a succinate buffer) may provide effective room temperature stability (e.g. at 25° C. and 60% relative humidity) while possibly conferring additional advantages—for example, the use of a succinic acid buffering agent or succinate buffer may contribute to reduced injection site reactions and associated pain compared with other buffered formulations.

The concentration of carbetocin in the liquid (composition e.g. aqueous composition) may be from 0.01 to 55 mg/mL, for example 0.01 to 50 mg/mL, for example 0.01 to 10 mg/mL, for example 0.01 to 1.5 mg/mL, preferably 0.05 to 0.5 mg/mL, for example 0.1 mg/mL. The concentration of carbetocin in the liquid (composition e.g. aqueous composition) may be, for example, 1 mg/mL, 10 mg/mL, 50 mg/mL etc.

The compositions of the invention may further comprise an anti-oxidant. The anti-oxidant may be any anti-oxidant commonly used in the art, for example any anti-oxidant approved for use as a pharmaceutical excipient. For example, the anti-oxidant may be methionine, EDTA, butylated hydroxy toluene, sodium metabisulfite etc. Preferably the anti-oxidant is present in an amount of 0.01% to 10% (w/v), for example 0.05% to 5% (w/v), most preferably 0.08% to 1% (w/v). Preferably the anti-oxidant is methionine, EDTA, or a combination of methionine and EDTA. For example, the antioxidant may be methionine and present in an amount of 0.1% w/v (or 1 mg/mL—see Example 2).

The composition may further comprise an isotonicity agent. Isotonicity agents, for example mannitol or NaCl, are well known in the art. Preferably the isotonicity agent is present in an amount sufficient to provide an isotonic composition (solution), for example in an amount of 0.01% to 10% (w/v). Preferably the isotonicity agent is mannitol. If the isotonicity agent is mannitol it may be present in an amount of 0.5% to 7.5% (w/v), more preferably 4.0% to 5.5% (w/v), for example 5.0% (w/v). If the isotonicity agent is mannitol it may be present in an amount of 0.05% to 7.5% (w/v). If the isotonicity agent is NaCl, it may be present in an amount of 0.05% to 1.2% (w/v), more preferably 0.08% to 1% (w/v), for example 0.9% (w/v). The isotonicity agent may be present in an amount of 0.1 to 100 mg/mL, for example 0.5 to 7 mg/mL, for example 1 to 5 mg/mL. For example, if the isotonicity agent is mannitol it may be present in an amount of 5 to 75 mg/mL, for example 40 to 55 mg/mL (see e.g. Table 3a). If the isotonicity agent is NaCl it may be present in an amount of 0.5 to 12 mg/mL, for example 8 to 10 mg/mL (see e.g. Table 3b), for example 7.5 mg/mL (see Example 6).

The composition may be for any route of drug administration, e.g. oral, rectal, buccal, nasal, vaginal, transdermal (e.g. patch technology); parenteral, intravenous, intramuscular or subcutaneous injection; intracisternal, intravaginal, intraperitoneal, local (powders, ointments or drops) or as a buccal or nasal spray. Preferably the composition is an injectable composition or injectable formulation. Injectable formulations can be supplied in any suitable container, e.g. ampoule, vial, pre-filled syringe, injection device (e.g. single use injection device such as that sold under the mark Uniject by Becton Dickinson), injection cartridge, ampoule, (multi-) dose pen and the like. Preferably the composition is for intramuscular administration (e.g. intramuscular injection) or intravenous administration (e.g. IV injection).

The composition may include an enhancer, an excipient which enhances the effective dose (e.g. enhances the effective dose following nasal administration). The enhancer may be any enhancer commonly used in the art, for example any enhancer approved for use as a pharmaceutical excipient. The enhancer may be, for example, methyl-β-cyclodextrin, Polysorbate 80, carboxymethylcellulose or hydroxypropylmethylcellulose.

The compositions of the invention may be for use in (or in the manufacture of medicaments for) the treatment or prevention of uterine atony. The compositions may be for use in the treatment or prevention of uterine atony following vaginal delivery of the infant. The compositions may be for use in the treatment or prevention of uterine atony following delivery of the infant by Caesarean section, for example delivery of the infant by Caesarean section under epidural or spinal anaesthesia. The compositions may be for use in the treatment or prevention of uterine atony, for example in a patient who is at risk of developing PPH. The compositions may be for use in (or in the manufacture of medicaments for) the treatment or prevention of bleeding (e.g. excessive bleeding) following vaginal delivery (of the infant). The compositions of the invention may be for use as a uteronic formulation. The compositions of the invention may be for (e.g. routine) administration following vaginal delivery of the infant.

According to the present invention in a further aspect there is provided a method of treatment or prevention of uterine atony (for example following vaginal delivery of the infant or delivery of the infant by Caesarean section, or in a patient who is at risk of developing PPH) or a method of treatment or prevention of excessive bleeding following vaginal delivery comprising, a step of administration to a patient in need thereof a composition as set out above.

It is preferred that the compositions of the invention do not include a quaternary amine compound, such as benzalkonium chloride. It is preferred that the compositions of the invention do not include a parahydroxybenzoate preservative, or a combination of parahydroxybenzoate preservative with a cosolvent. It is preferred that the compositions of the invention have a content of divalent metal ions of less than 2 mM, for example 0.195 mM or less, for example 0.1 nM or less. It is preferred that compositions of the invention do not include a solubilizer. It is preferred that compositions of the invention do not include methyl-β-cyclodextrin.

In another aspect of the invention, there are provided stabilised formulations of carbetocin or other pharmaceutically active compounds (e.g. other pharmaceutically active peptides or pharmaceutically active small molecules). Thus, according to the invention in a further aspect there is provided a liquid (e.g. aqueous) composition comprising: a pharmaceutically active compound or salt thereof; and an anti-oxidant; wherein the pH of the composition is from 5.0 to 6.0. The pH of the composition may be from 5.1 to 6.0, for example from 5.2 to 6, for example from 5.26 to 6. The pH of the composition may be from 5.15 to 5.75, for example from 5.2 to 5.65. The pH of the composition may be from 5.0 to 5.9, for example from 5.1 to 5.9, for example 5.2 to 5.8. The pH of the composition may be from 5.26 to 5.8, for example from 5.26 to 5.75, for example from 5.26 to 5.7, for example from 5.26 to 5.65, for example 5.4 to 5.65. The pharmaceutically active compound may be carbetocin. The composition may be for nasal administration. The pharmaceutically active compound may be a compound having the formula (I) or solvate or pharmaceutically acceptable salts thereof:

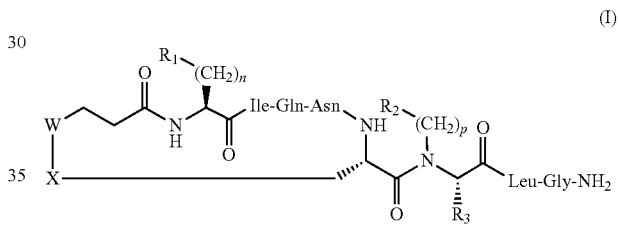

(I)

wherein: n is selected from 0, 1 and 2; p is selected from 0, 1, 2, 3, 4, 5 and 6; $R_1$ is selected from aryl optionally substituted with at least one OH, F, Cl, Br, alkyl or O-alkyl substituent; $R_2$ is selected from $R_4$, H, alkyl, cycloalkyl, aryl and 5- and 6-membered heteroaromatic ring systems; $R_3$ is selected from H and a covalent bond to $R_2$, when $R_2$ is $R_4$, to form a ring structure; $R_4$ is $C_{1-6}$ alkylene moiety substituted with at least one O-alkyl, S-alkyl or OH substituent; W and X are each independently selected from $CH_2$ and S, but may not both be $CH_2$; alkyl is selected from $C_{1-6}$ straight and $C_{4-8}$ branched chain alkyl and optionally has at least one hydroxyl substituent; aryl is selected from phenyl and mono- or poly-substituted phenyl; with the proviso that when $R_2$ is H, p is 1, $R_3$ is H, n is 1 and W and X are both S, $R_1$ is not 4-hydroxyphenyl. In the above and herein, aryl denotes an aromatic group selected from phenyl and mono- or poly-substituted phenyl; the substituent moieties, if present, may be selected from fluorine (F), chlorine (Cl) and bromine (Br) atoms and alkyl, hydroxy (—OH), alkoxy (—O-alkyl) and alkylthio (—S-alkyl). Preferably the pharmaceutically active compound is a compound according to formula (I) above with the proviso that when $R_2$ is H, p is 0, $R_3$ is H, n is 1 and W and X are both S, $R_1$ is not 4-hydroxyphenyl. These compounds, their medical uses and their methods of their preparation are disclosed in WO2009/122285 (International Patent Application No. PCT/IB2009/005351) of Ferring B.V.

Preferably the pharmaceutically active compound is carba-1-[4-FBzlGly$^7$]dOT, wherein 4-FBzlGly is N-(4-fluorobenzyl)glycine. Carba-1-[4-FBzIGly⁷]dOT is an oxytocin analogue also known as FE 202767. FE 202767 has the structure of formula (II):

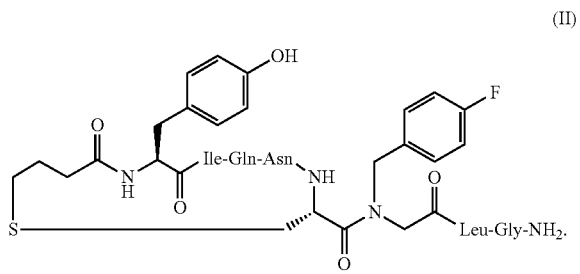

FE 202767 is a selective oxytocin receptor agonist being evaluated for clinical use. FE 202767 of formula (II), some medical uses thereof, and methods of its preparation are disclosed in WO2009/122285. FE202767 is Example 49 of WO2009/122285 (International Patent Application No. PCT/IB2009/005351) of Ferring B.V.

Peptidic oxytocin agonists such as those disclosed in WO2009/122285 are expected to be delivered by the intranasal route (i.e. intranasal administration). Intranasal formulations of this type are generally contained in (and administered using) spray devices, where the drug remains in solution (e.g. at a concentration of active compound of 0.05-2 mg/mL) under inert atmosphere for an extended period of time (up to 2 years). There is therefore a need for room temperature stable formulations of oxytocin agonists/analogues such as carba-1-[4-FBzIGly⁷]dOT (FE 202767), e.g. to avoid requirement for refrigeration.

The composition may comprise a buffering agent, for example acetic acid, adipic acid, citric acid, maleic acid, succinic acid or (e.g. sodium) phosphate. The composition may include a single buffering agent. The composition may include more than one buffering agent (e.g. may comprise citric acid and (e.g. sodium) phosphate). The composition may comprise a buffer (solution), for example, a citrate buffer (solution), comprising citric acid and a citrate (e.g. sodium citrate); a succinate buffer (solution) comprising succinic acid and a succinate (e.g. sodium succinate), an acetate buffer (solution) comprising acetic acid and an acetate (e.g. sodium acetate); a citrate/phosphate buffer (solution) comprising citric acid and phosphate; or a phosphate buffer (solution). It is preferred, however, that if the pharmaceutically active compound is 1-deamino-8-D-arginine vasopressin (desmopressin) the buffering agent is not malic acid (and/or the composition does not include malic acid buffer).

The concentration of the pharmaceutically acceptable compound in the liquid (aqueous) composition may be, for example, 0.01 to 5 mg/mL.

The concentration of carbetocin in the liquid (aqueous) composition may be from 0.01 to 55 mg/mL, for example 0.01 to 50 mg/mL, for example 0.01 to 10 mg/mL, for example 0.01 to 1.5 mg/mL, preferably 0.05 to 0.5 mg/mL, for example 0.1 mg/mL. The concentration of carbetocin in the liquid (composition e.g. aqueous composition) may be, for example, 1 mg/mL, 10 mg/mL, 50 mg/mL etc.

The concentration of the compound of formula (II) in the liquid (aqueous) composition may be from 0.01 to 4 mg/mL, for example 0.05 to 2 mg/mL, more preferably 0.1 to 1.4 mg/mL, most preferably 0.2 to 0.7 mg/mL.

The compositions of this aspect of the invention comprise an anti-oxidant. The anti-oxidant may be any anti-oxidant commonly used in the art, for example any anti-oxidant approved for use as a pharmaceutical excipient. For example, the anti-oxidant may be methionine, EDTA, butylated hydroxy toluene, sodium metabisulfite etc. Preferably the anti-oxidant is present in an amount of 0.01% to 10% (w/v), for example 0.05% to 5% (w/v), most preferably 0.08% to 1% (w/v). Preferably the anti-oxidant is methionine, EDTA, or a combination of methionine and EDTA. In an example, the antioxidant is methionine and is present in an amount of 0.5% w/v. In an example, the antioxidant is EDTA and is present in an amount of 0.1% w/v.

The composition may further comprise an isotonicity agent. Isotonicity agents, for example mannitol or NaCl, are well known in the art. Preferably the isotonicity agent is present in an amount sufficient to provide an isotonic composition (solution), for example in an amount of 0.01% to 10% (w/v). Preferably the isotonicity agent is mannitol. If the isotonicity agent is mannitol it may be present in an amount of 0.5% to 7.5% (w/v), more preferably 4.0% to 5.5% (w/v), for example 5.0% (w/v). If the isotonicity agent is mannitol it may be present in an amount of 0.05% to 7.5% (w/v). If the isotonicity agent is NaCl it may be present in an amount of 0.05% to 1.2% (w/v), more preferably 0.08% to 1% (w/v), for example 0.9% (w/v). The isotonicity agent may be present in an amount of 0.1 to 100 mg/mL, for example 0.5 to 7 mg/mL, for example 1 to 5 mg/mL. For example, if the isotonicity agent is mannitol it may be present in an amount of 5 to 75 mg/mL, for example 40 to 55 mg/mL. If the isotonicity agent is NaCl it may be present in an amount of 0.5 to 12 mg/mL, for example 8 to 10 mg/mL.

The composition may be for any route of drug administration, e.g. oral, rectal, buccal, nasal, vaginal, transdermal (e.g. patch technology); parenteral, intravenous, intramuscular or subcutaneous injection; intracisternal, intravaginal, intraperitoneal, local (powders, ointments or drops) or as a buccal or nasal spray. Preferably the composition is for nasal administration, e.g. is a nasal spray. As indicated above, compositions suitable for intranasal administration are expected to remain stable in solution at room temperature for an extended period of time.

The composition may include an enhancer, an excipient which enhances the effective dose (e.g. enhances the effective dose following nasal administration). The enhancer may be any enhancer commonly used in the art, for example any enhancer approved for use as a pharmaceutical excipient. The enhancer may be, for example, methyl-β-cyclodextrin, Polysorbate 80, carboxymethylcellulose or hydroxypropylmethylcellulose.

It is preferred that the compositions of the invention do not include a quaternary amine compound, such as benzalkonium chloride. It is preferred that the compositions of the invention do not include a parahydroxybenzoate preservative, or a combination of parahydroxybenzoate preservative with a cosolvent. It is preferred that the compositions of the invention have a content of divalent metal ions of less than 2 mM, for example 0.195 mM or less, for example 0.1 nM or less. It is preferred that compositions of the invention do not include a solubilizer. It is preferred that compositions of the invention do not include methyl-β-cyclodextrin.

According to the invention in a further aspect there is provided a liquid (e.g. aqueous) composition comprising: a pharmaceutically active compound according to formula (II):

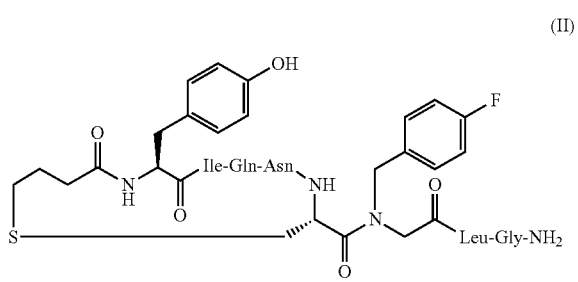

(II)

or (pharmaceutically acceptable) salt thereof; wherein the pH of the composition is from 5.0 to 6.0. The pH of the composition may be from 5.0 to 5.9, for example from 5.1 to 5.9, for example 5.2 to 5.8. The pH of the composition may be from 5.1 to 6.0, for example from 5.2 to 6, for example from 5.26 to 6. The pH of the composition may be from 5.15 to 5.75, for example from 5.2 to 5.65. The pH of the composition may be from 5.26 to 5.8, for example from 5.26 to 5.75, for example from 5.26 to 5.7, for example from 5.26 to 5.65, for example 5.4 to 5.65. Preferably, the liquid (e.g. aqueous) composition comprises a pharmaceutically active compound according to formula (II):

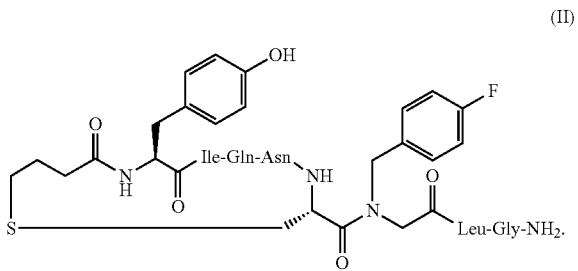

(II)

The composition may be for any route of drug administration, e.g. oral, rectal, buccal, nasal, vaginal, transdermal (e.g. patch technology); parenteral, intravenous, intramuscular or subcutaneous injection; intracisternal, intravaginal, intraperitoneal, local (powders, ointments or drops) or as a buccal or nasal spray. Preferably the composition is for nasal administration, e.g. is a nasal spray. As indicated above, compositions suitable for intranasal administration are expected to remain stable in solution at room temperature for an extended period of time. Remarkably, the applicants have found that compositions of the compound of formula (II) above may provide such stability at pH values which are particularly suitable for nasal administration, without requirement for inclusion of an anti-oxidant (see Example 7).

The composition may comprise a buffering agent, for example acetic acid, adipic acid, citric acid, maleic acid, succinic acid or (e.g. sodium) phosphate. The composition may include a single buffering agent. The composition may include more than one buffering agent (e.g. may comprise citric acid and (e.g. sodium) phosphate). The composition may comprise a buffer (solution), for example, a citrate buffer (solution), comprising citric acid and a citrate (e.g. sodium citrate); a succinate buffer (solution) comprising succinic acid and a succinate (e.g. sodium succinate), an acetate buffer (solution) comprising acetic acid and an acetate (e.g. sodium acetate); a citrate/phosphate buffer (solution) comprising citric acid and phosphate; or a phosphate buffer (solution).

Preferably the pharmaceutical composition comprises a citrate/phosphate buffer and the pH is from 5.1 to 6.0, for example from 5.2 to 6, for example from 5.26 to 6.

Preferably the pharmaceutical composition comprises a succinate buffer or a citrate buffer and the pH is from 5.0 to 5.9, for example 5.0 to 5.8, for example from 5 to 5.7.

The concentration of the compound of formula (II) in the liquid (aqueous) composition may be from 0.01 to 4 mg/mL, for example 0.05 to 2 mg/mL, more preferably 0.1 to 1.4 mg/mL, most preferably 0.2 to 0.7 mg/mL.

The compositions of this aspect of the invention further comprise an anti-oxidant. The anti-oxidant may be any anti-oxidant commonly used in the art, for example any anti-oxidant approved for use as a pharmaceutical excipient. For example, the anti-oxidant may be methionine, EDTA, butylated hydroxy toluene, sodium metabisulfite etc. Preferably the anti-oxidant is present in an amount of 0.01% to 10% (w/v), for example 0.05% to 5% (w/v), most preferably 0.08% to 1% (w/v). Preferably the anti-oxidant is methionine, EDTA, or a combination of methionine and EDTA. In an example, the antioxidant is methionine and is present in an amount of 0.5% w/v. In an example, the antioxidant is EDTA and is present in an amount of 0.1% w/v.

The composition may further comprise an isotonicity agent. Isotonicity agents, for example mannitol or NaCl, are well known in the art. Preferably the isotonicity agent is present in an amount sufficient to provide an isotonic composition (solution), for example in an amount of 0.01% to 10% (w/v). Preferably the isotonicity agent is mannitol. If the isotonicity agent is mannitol it may be present in an amount of 0.5% to 7.5% (w/v), more preferably 4.0% to 5.5% (w/v), for example 5.0% (w/v). If the isotonicity agent is mannitol it may be present in an amount of 0.05% to 7.5% (w/v). If the isotonicity agent is NaCl it may be present in an amount of 0.05% to 1.2% (w/v), more preferably 0.08% to 1% (w/v), for example 0.9% (w/v). The isotonicity agent may be present in an amount of 0.1 to 100 mg/mL, for example 0.5 to 7 mg/mL, for example 1 to 5 mg/mL. For example, if the isotonicity agent is mannitol it may be present in an amount of 5 to 75 mg/mL, for example 40 to 55 mg/mL. If the isotonicity agent is NaCl it may be present in an amount of 0.5 to 12 mg/mL, for example 8 to 10 mg/mL.

It is preferred that the compositions of the invention do not include a quaternary amine compound, such as benzalkonium chloride. It is preferred that the compositions of the invention do not include a parahydroxybenzoate preservative, or a combination of parahydroxybenzoate preservative with a cosolvent. It is preferred that the compositions of the invention have a content of divalent metal ions of less than 2 mM, for example 0.195 mM or less, for example 0.1 nM or less. It is preferred that compositions of the invention do not include a solubilizer. It is preferred that compositions of the invention do not include methyl-β-cyclodextrin.

According to the present invention in a further aspect, there is provided a method of treatment or prevention of uterine atony [for example, treatment or prevention of uterine atony following vaginal delivery of the infant, treatment or prevention of uterine atony following delivery of the infant by Caesarean section, for example delivery of the infant by Caesarean section under epidural or spinal anaesthesia, or treatment or prevention of uterine atony in a patient who is at risk of developing PPH], or a method of treatment or prevention of bleeding (e.g. excessive bleeding) following vaginal delivery (of the infant), comprising: administration to a patient in need thereof a liquid (e.g. aqueous) pharmaceutical composition comprising carbetocin or a pharmaceutically active salt thereof; wherein the pH of the composition is from 5.0 to 6.0. The pH of the composition may be from 5.1 to 6.0, for example from 5.2 to 6, for example from 5.26 to 6. The pH of the composition may be from 5.15 to 5.75, for example from 5.2 to 5.65. The pH of the composition may be from 5.26 to 5.8, for example from 5.26 to 5.75, for example from 5.26 to 5.7, for example from 5.26 to 5.65, for example 5.4 to 5.65.

According to the present invention in a further aspect, there is provided a kit of parts comprising: a liquid (e.g. aqueous) pharmaceutical composition comprising carbetocin or a pharmaceutically active salt thereof wherein the pH of the composition is from 5.0 to 6.0; and a container [e.g. ampoule, vial, pre-filled syringe, injection device (e.g. single use injection device such as that sold under the mark Uniject by Becton Dickinson), injection cartridge, ampoule, multi-dose pen] for the composition, optionally with separate injection means (e.g. if required for administration), optionally with instructions for administration of the composition. The pH of the composition may be from 5.1 to 6.0, for example from 5.2 to 6, for example from 5.26 to 6. The pH of the composition may be from 5.15 to 5.75, for example from 5.2 to 5.65. The pH of the composition may be from 5.26 to 5.8, for example from 5.26 to 5.75, for example from 5.26 to 5.7, for example from 5.26 to 5.65, for example 5.4 to 5.65.

According to the present invention in a further aspect, there is provided a kit of parts comprising: a liquid (e.g. aqueous) pharmaceutical composition comprising a pharmaceutically active compound (e.g. carbetocin) or salt thereof and optionally an anti-oxidant, wherein the pH of the composition is from 5.0 to 6.0; and a container (e.g. vial, pre-filled syringe, injection device [e.g. single use pre-filled injection device such as that sold under the mark Uniject by Becton Dickinson), injection cartridge, ampoule, multi-dose pen] for the composition, optionally with separate injection means (e.g. if required for administration), optionally with instructions for administration of the composition. The pH of the composition may be from 5.1 to 6.0, for example from 5.2 to 6, for example from 5.26 to 6. The pH of the composition may be from 5.15 to 5.75, for example from 5.2 to 5.65. The pH of the composition may be from 5.26 to 5.8, for example from 5.26 to 5.75, for example from 5.26 to 5.7, for example from 5.26 to 5.65, for example 5.4 to 5.65.

According to the present invention in a further aspect, there is provided a method of treatment or prevention of compromised lactation conditions, labour induction impairment, uterine atony conditions, excessive bleeding, inflammation, pain, abdominal pain, back pain, male and female sexual dysfunction, irritable bowel syndrome (IBS), constipation, gastrointestinal obstruction, autism, stress, anxiety, depression, anxiety disorder, surgical blood loss, post-partum haemorrhage, wound healing, infection, mastitis, placenta delivery impairment, osteoporosis, and a method for the diagnosis of cancer and placental insufficiency, comprising: administration to a patient in need thereof a liquid (e.g. aqueous) pharmaceutical composition comprising a pharmaceutical compound according to formula (I) or (II) as defined above or a pharmaceutically active salt thereof; wherein the pH of the composition is from 5.0 to 6.0. According to the present invention in a still further aspect, there is provided a liquid (e.g. aqueous) pharmaceutical composition comprising a pharmaceutical compound according to formula (I) or (II) as defined above or a pharmaceutically active salt thereof; wherein the pH of the composition is from 5.0 to 6.0; for use in (or in the manufacture of a medicament for) the treatment or prevention of compromised lactation conditions, labour induction impairment, uterine atony conditions, excessive bleeding, inflammation, pain, abdominal pain, back pain, male and female sexual dysfunction, irritable bowel syndrome (IBS), constipation, gastrointestinal obstruction, autism, stress, anxiety, depression, anxiety disorder, surgical blood loss, post-partum haemorrhage, wound healing, infection, mastitis, placenta delivery impairment, osteoporosis, or for use in (or in the manufacture of a substance for) the diagnosis of cancer or placental insufficiency. The pH of the composition may be from 5.1 to 6.0, for example from 5.2 to 6, for example from 5.26 to 6. The pH of the composition may be from 5.0 to 5.9, for example from 5.1 to 5.9, for example 5.2 to 5.8. The pH of the composition may be from 5.15 to 5.75, for example from 5.2 to 5.65. The pH of the composition may be from 5.26 to 5.8, for example from 5.26 to 5.75, for example from 5.26 to 5.7, for example from 5.26 to 5.65, for example 5.4 to 5.65.

According to the present invention in a further aspect, there is provided a kit of parts comprising: a liquid (e.g. aqueous) pharmaceutical composition comprising carbetocin or a pharmaceutically active compound according to formula (II):

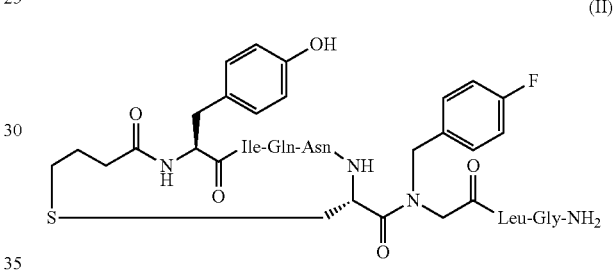

or a pharmaceutically active salt thereof wherein the pH of the composition is from 5.0 to 6.0; and a container [e.g. ampoule, vial, pre-filled syringe, injection device (e.g. single use injection device such as that sold under the mark Uniject by Becton Dickinson), injection cartridge, ampoule, multi-dose pen] for the composition, optionally with separate injection means (e.g. if required for administration), optionally with instructions for administration of the composition. The pH of the composition may be from 5.0 to 5.9, for example from 5.1 to 5.9, for example 5.2 to 5.8. The pH of the composition may be from 5.1 to 6.0, for example from 5.2 to 6, for example from 5.26 to 6. The pH of the composition may be from 5.15 to 5.75, for example from 5.2 to 5.65. The pH of the composition may be from 5.26 to 5.8, for example from 5.26 to 5.75, for example from 5.26 to 5.7, for example from 5.26 to 5.65, for example 5.4 to 5.65.

According to the present invention in a further aspect, there is provided a kit of parts comprising: a liquid (e.g. aqueous) pharmaceutical composition comprising a pharmaceutically active compound (e.g. carbetocin, a compound of formula (I) or (II) above) or salt thereof and optionally an anti-oxidant, wherein the pH of the composition is from 5.0 to 6.0; and a container (e.g. vial, pre-filled syringe, injection device [e.g. single use pre-filled injection device such as that sold under the mark Uniject by Becton Dickinson), injection cartridge, ampoule, multi-dose pen] for the composition, optionally with separate injection means (e.g. if required for administration), optionally with instructions for administration of the composition. The pH of the composition may be from 5.1 to 6.0, for example from 5.2 to 6, for example from 5.26 to 6. The pH of the composition may be from 5.0 to 5.9, for example from 5.1 to 5.9, for example 5.2 to 5.8. The pH of the composition may be from 5.15 to 5.75, for example from 5.2 to 5.65. The pH of the composition may be from 5.26 to 5.8, for example from 5.26 to 5.75, for example from 5.26 to 5.7, for example from 5.26 to 5.65, for example 5.4 to 5.65.

DETAILED DESCRIPTION OF THE INVENTION

The present invention will now be illustrated with reference to the attached drawings in which:

FIG. 1 shows a UPLC chromatogram of an impurity mix of carbetocin and degradation products;

ANALYTICAL METHOD

Figure 1A:
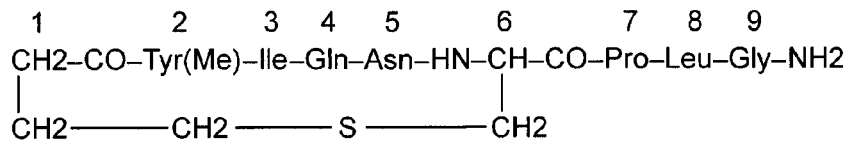
FIG. 1a shows the chemical formulae of carbetocin and degradation products.
Figure 1A:
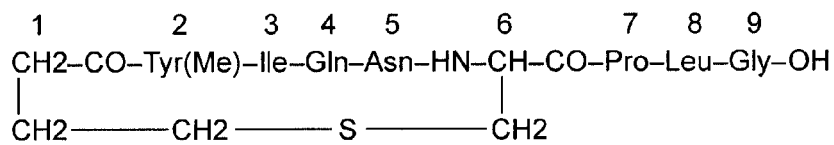
Figure 1A:
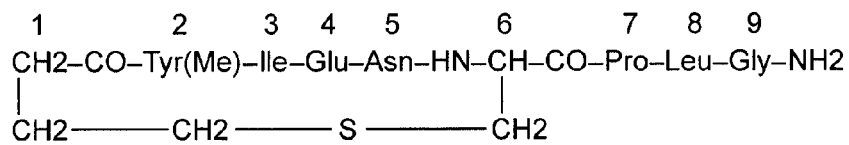
Figure 1A:
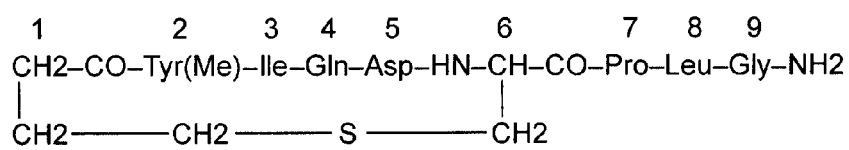
Figure 1A:
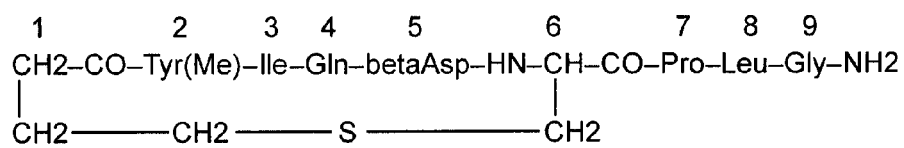
Figure 1A:
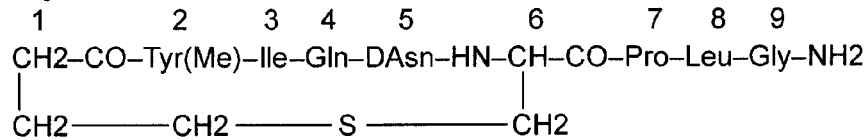
Figure 1A:
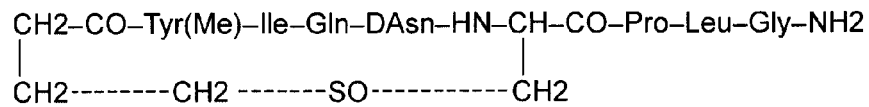

This is the analytical method for the carbetocin examples (Examples 1 to 6), below.

All solutions were analysed on a Waters Acquity UPLC (Ultra-high Pressure Liquid chromatography) system using isocratic conditions. The Mobile phase was 20% acetonitrile (JT Baker, Ultra Gradient Grade) in 5 mM unbuffered ammonium acetate (Fluka, Ultra ≥99.0%). The column was a Waters Acquity UPLC BEH Shield RP18, 2.1*100 mm, 1.7 μm (Flow: 0.5 ml/min, Column Temp: 50° C.). The injection volume was 20 μl. Detection was performed by UV at 220 nm. The different impurities were evaluated as area % of total area.

FIG. 1 shows a chromatogram of an impurity mix of carbetocin and its degradation products. The solution contained, carbetocin, the hydrolysis products [Gly$^9$OH], [Asp$^5$] and [Glu$^4$]carbetocin, the oxidation products sulfoxide I and sulfoxide II-carbetocin, the alkaline degradation products [β Asp$^5$] and [D-Asn$^5$]carbetocin and the synthesis related impurity [D-Cys$^6$]carbetocin. The chemical formulae of carbetocin and the degradation products (hydrolysis products, oxidation products and alkaline degradation products) are shown in FIG. 1a. The "[Glu$^4$]carbetocin" type nomenclature is well known in the art. The resolutions between all peaks were ≥2.0.

Example 1

Formulation Antioxidant Study (Constant pH)

5.0 grams of D(−)-Mannitol (Ph Eur, Prolabo) was dissolved in 1000 ml of milliQ-water. This solution was adjusted with acetic acid (Ph. Eur., Merck) to pH 5.2. This solution was then divided into four 200 ml aliquots. To aliquot 1, 0.2 gram of EDTA disodium, dihydrate (Fluka) was added and dissolved. To aliquot 2, 1.0 gram of L-methionine (Sigma, non-animal source) was added and dissolved. To aliquot 3, 0.2 gram of EDTA disodium, dihydrate and 1.0 g of L-methionine was added and dissolved. Nothing was added to aliquot 4. The pH of aliquots 1-3 was adjusted with acetic acid to pH 5.2±0.1. 1 mg of carbetocin (Polypeptide Laboratories) was transferred to four 10 ml volumetric flasks. Aliquots 1-4 were used to dissolve the substance and for dilution to volume (0.1 mg/ml carbetocin). The solutions were transferred to 25 ml blue cap flasks, and placed in a cabinet at 40° C. and 75% RH. A sample of the current PABAL® formulation, pH 3.9 (measured), was placed in the same cabinet for comparison.

Figure 2:
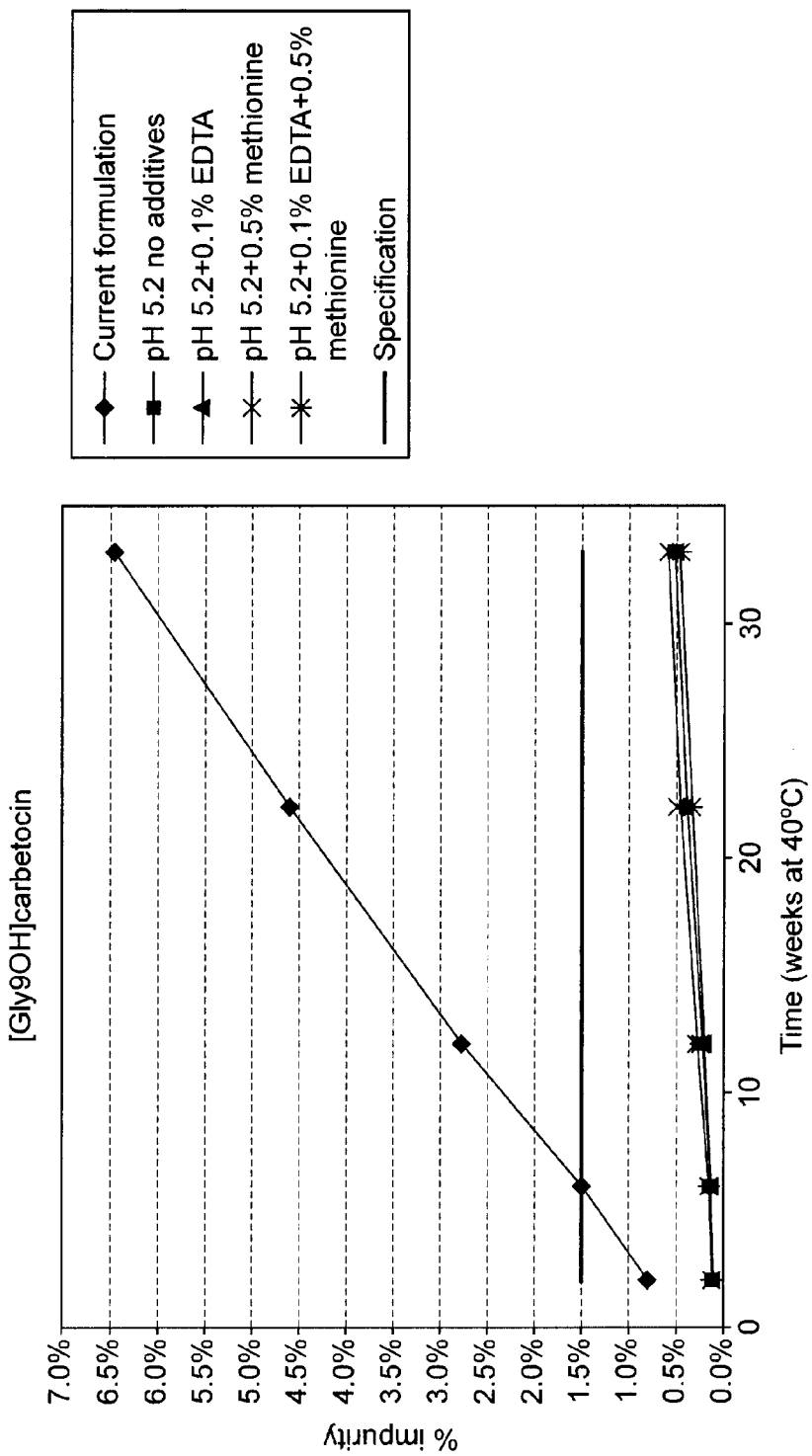
FIG. 2 shows the content of degradation (hydrolysis) product [Gly$^9$OH]carbetocin (see FIG. 1a) in the antioxidant study samples as a function of time (constant pH)
Figure 3:
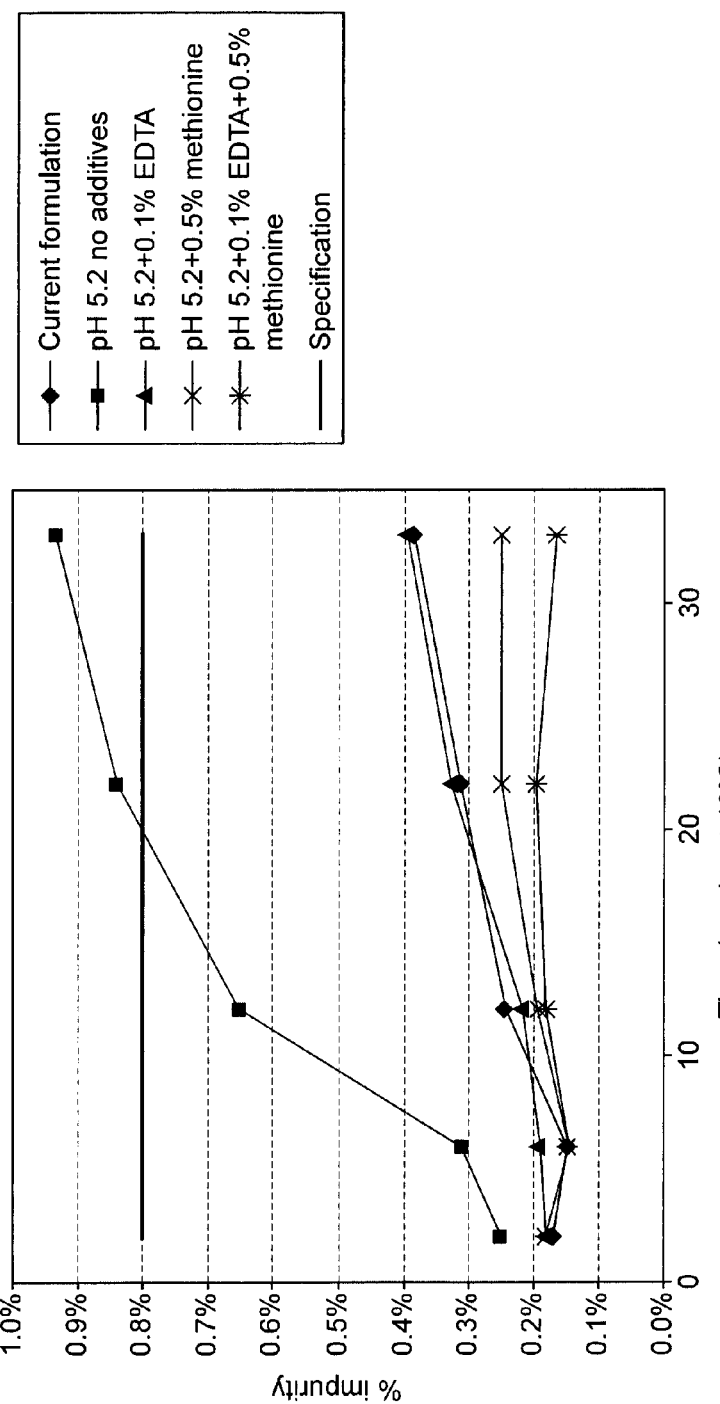
FIG. 3 shows the content of degradation (oxidation) product sulfoxide II carbetocin (see FIG. 1a) in the antioxidant study samples as a function of time (constant pH)

The solutions were analysed after 2, 6, 12, 22 and 33 weeks at 40° C. The largest impurities of this study was found to be the hydrolysis product [Gly$^9$OH]carbetocin and the oxidation product [sulfoxide II]carbetocin. The pH in this study (pH 5.2) was not high enough to start any alkaline degradation of carbetocin. The content % (w/w) of the major impurity formed by hydrolysis, [Gly$^9$OH]carbetocin, and by oxidation, sulfoxide II-carbetocin, are shown in FIGS. 2 and 3. The product specification allowed for each impurity is also plotted in each figure as a reference. Thus it can be seen from FIG. 2 that if the concentration of [Gly$^9$OH] carbetocin increases above 1.5% the sample is "out of specification", that is the sample has degraded such that is no longer suitable for administration.

As shown in FIG. 2, the antioxidant study (constant pH) showed that the formation of hydrolysis products, mainly [Gly$^9$OH]carbetocin, was very fast in the current PABAL formulation (pH 3.9). With regard to the content of [Gly$^9$OH]carbetocin the current formulation was quickly out-of-specification (>1.5%), after 6 weeks at 40° C. All formulations at pH 5.2 were well below the specification limit after 33 weeks at 40° C. (0.4-0.6%), indicating that these formulations are stable for at least 6 months at 40° C. and 75% RH, which is generally accepted to indicate a likely stability for at least 24 months at 25° C. and 60% RH (i.e. a stable RT formulation) The results applied for all three hydrolysis products. In FIG. 3, the addition of antioxidant was shown to be very effective in slowing down the oxidation of carbetocin, despite the increased pH of the formulations. The formulation at pH 5.2 that did not contain any additives was out-of-specification (>0.8%) with regard to the content of sulfoxide II-carbetocin after approx 20 weeks at 40° C. The formulations containing methionine or EDTA were all well below the specification limit after 33 weeks (0.2-0.4%). The formulation containing a combination of EDTA and methionine did not show any increase of oxidation products at all, compared to the levels found in the substance batch. Due to the low pH, the current formulation was not prone to degradation by oxidation (pH 3.9). The results are shown in numerical form in the following table (Table 1).

TABLE 1

Individual and sum of degradation products (%) after 33 weeks at 40° C. (constant pH).

| Formulation | Gly$^9$OH | Asp$^5$ | Glu$^4$ | Sulfoxide I | Sulfoxide II | βAsp5 | D-Asn$^5$ | Sum of impurities |
|---|---|---|---|---|---|---|---|---|
| Current formulation | 6.43 | 1.15 | 5.41 | 0.42 | 0.38 | 0.13 | 0.15 | 16.4 |
| Mannitol pH 5.2 | 0.53 | 0.14 | 0.42 | 0.51 | 0.93 | 0.13 | 0.12 | 3.5 |
| Mannitol pH 5.2 + methionine | 0.63 | 0.20 | 0.51 | 0.14 | 0.25 | 0.15 | 0.16 | 3.2 |
| Mannitol pH 5.2 + EDTA | 0.52 | 0.15 | 0.38 | 0.31 | 0.39 | 0.15 | 0.10 | 2.9 |
| Mannitol pH 5.2 + methionine + EDTA | 0.44 | 0.13 | 0.35 | 0.10 | 0.16 | 0.19 | 0.17 | 2.4 |

Table 1 includes the sum of degradation products for all samples, and after 33 weeks the effect of EDTA is clearer. Further, the sample containing both methionine and EDTA is clearly better than the others. The evidence points to a linear degradation: assuming this is indeed the case, the mannitol pH 5.2+methionine+EDTA sample is likely to be in specification—i.e. suitable for use—for a remarkable 86 weeks at 40° C. This is based, as is well known in the art, on a linear extrapolation of the increase in impurity over time to determine when the amount of impurity would be sufficiently high for the formulation to be "out of specification".

Example 2

Formulation pH Study (Constant Antioxidant)

1.2 grams of succinic acid (Sigma-Aldrich, 99%) and 1.0 g of L-methionine (Sigma, non-animal source) were dissolved in 1000 ml of milliQ water (10 mM). This solution was adjusted, in aliquots, with diluted NaOH (Ph. Eur., Merck) to pH 4.0, 4.5, 5.2, 5.65, 6.1, 6.5 and 7.0. 55 mg of carbetocin (Polypeptide Laboratories) was dissolved in 50 ml of milliQ water (1.1 mg/ml). 1.0 ml of the carbetocin solution (1.1 mg/ml) was mixed with 10 ml of each buffer (0.1 mg/ml carbetocin). 0.55 g of mannitol (5%) was added to each solution and dissolved. The solutions were transferred to 15 ml glass vials with screw lid and placed in a 40° C. cabinet at 75% RH.

Figure 4:
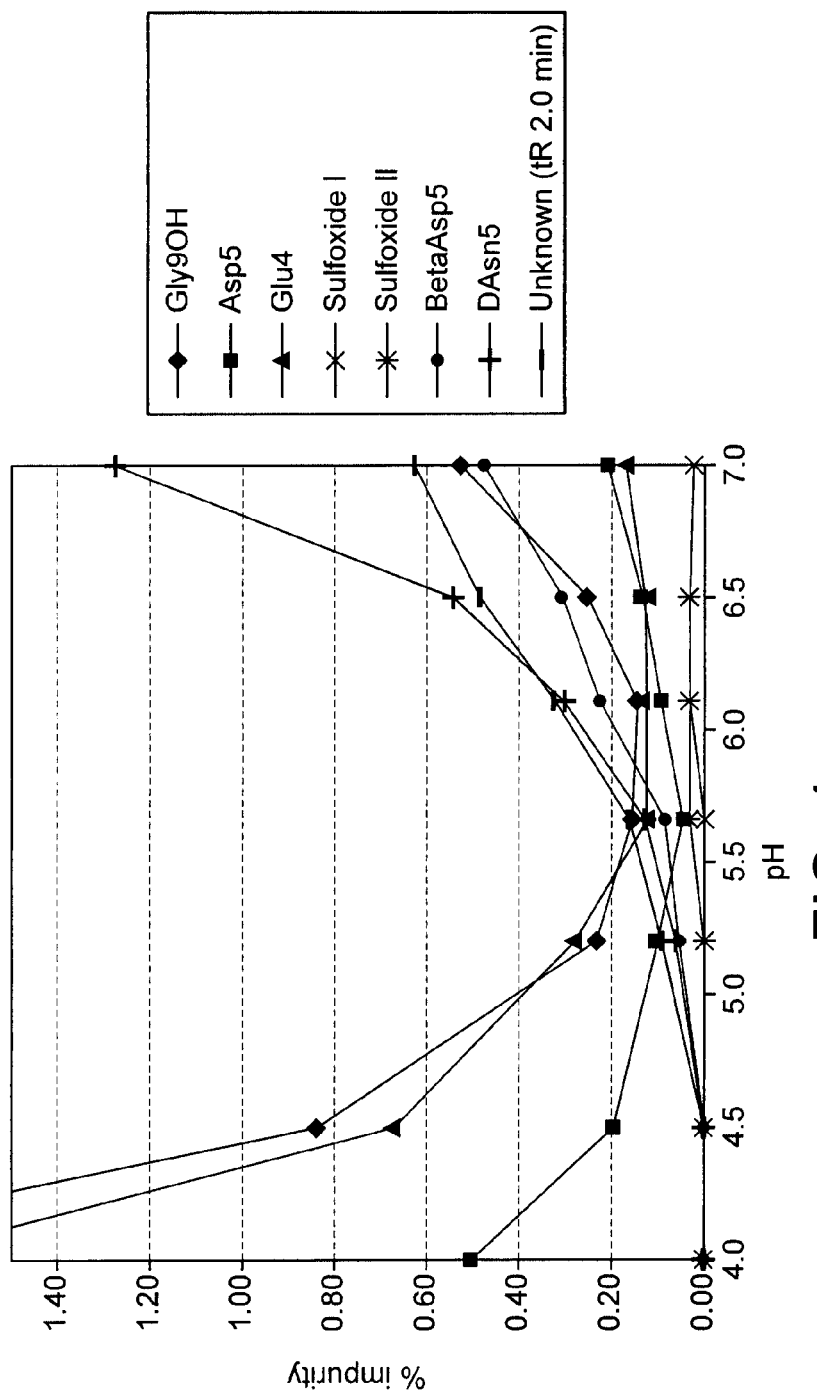
FIG. 4 shows individual degradation products at different pH (pH study, constant antioxidant)
Figure 5:
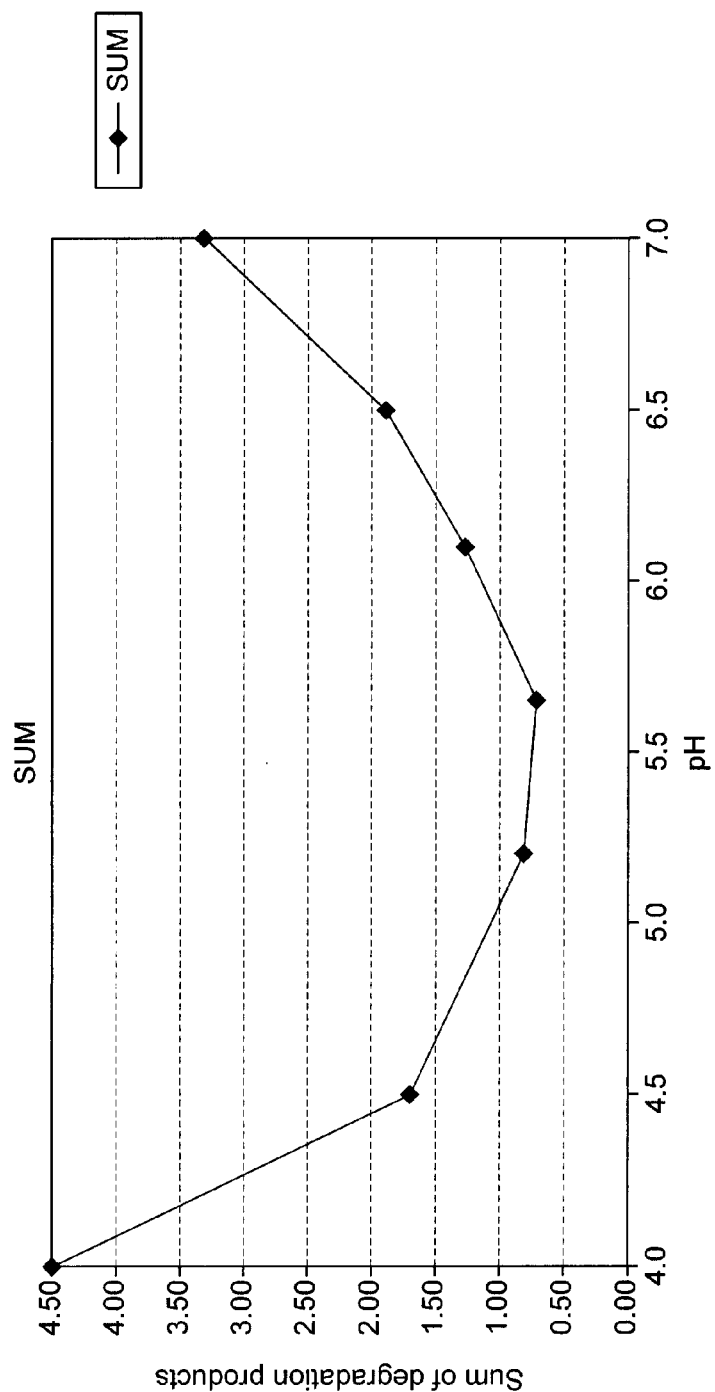
FIG. 5 shows the sum of degradation products at different pH (pH study, constant antioxidant)

The solutions were analysed after 12 and 52 weeks at 40° C. The content of the individual degradation products and the sum of degradation products is presented in Tables 2a and 2b and FIGS. 4 and 5.

TABLE 2a

Individual and sum of degradation products (%) at different pH after 12 weeks at 40° C. (pH study, constant antioxidant).

| Sample pH | Hydrolysis products | | | Oxidation products | | Alkaline impurities | | Unknown | Sum |
|---|---|---|---|---|---|---|---|---|---|
| | [Gly$^9$OH] | [Asp$^5$] | [Glu$^4$] | Sulfoxide I | Sulfoxide II | [D-Asn$^5$] | [βAsp$^5$] | 2.0 min | |
| 4.0 | 2.22 | 0.50 | 1.78 | N.D | N.D | N.D. | N.D. | N.D. | 4.50 |
| 4.5 | 0.84 | 0.19 | 0.67 | N.D | N.D | N.D. | N.D. | N.D. | 1.70 |
| 5.2 | 0.23 | 0.10 | 0.27 | N.D | N.D | 0.06 | 0.05 | 0.09 | 0.80 |
| 5.65 | 0.15 | 0.04 | 0.12 | N.D | 0.03 | 0.12 | 0.08 | 0.16 | 0.70 |
| 6.1 | 0.14 | 0.09 | 0.13 | 0.03 | 0.03 | 0.30 | 0.22 | 0.32 | 1.26 |
| 6.5 | 0.25 | 0.13 | 0.12 | 0.03 | 0.03 | 0.54 | 0.30 | 0.48 | 1.88 |
| 7.0 | 0.52 | 0.20 | 0.17 | 0.02 | 0.02 | 1.27 | 0.47 | 0.62 | 3.29 |

TABLE 2b

Individual and sum of degradation products (%) at different pH after 52 weeks at 40° C. (pH study, constant antioxidant).

| Sample pH | Hydrolysis products | | | Oxidation products | | Alkaline impurities | | Unknown | Sum |
|---|---|---|---|---|---|---|---|---|---|
| | [Gly$^9$OH] | [Asp$^5$] | [Glu$^4$] | Sulfoxide I | Sulfoxide II | [D-Asn$^5$] | [βAsp$^5$] | 2.0 min | |
| 4.0 | 7.55 | 1.09 | 6.23 | 0.04 | 0.07 | 0.00 | 0.19 | 0.94 | 19.3 |
| 4.5 | 2.92 | 0.57 | 2.49 | 0.04 | 0.05 | 0.00 | 0.19 | 0.40 | 7.8 |
| 5.2 | 0.78 | 0.26 | 0.72 | 0.05 | 0.14 | 0.26 | 0.25 | 0.22 | 3.6 |
| 5.65 | 0.48 | 0.22 | 0.52 | 0.02 | 0.02 | 0.45 | 0.40 | 0.40 | 3.8 |
| 6.1 | 0.56 | 0.35 | 0.34 | 0.08 | 0.11 | 1.06 | 0.73 | 0.77 | 5.9 |

TABLE 2b-continued

Individual and sum of degradation products (%) at different pH after 52 weeks at 40° C. (pH study, constant antioxidant).

| Sample pH | Hydrolysis products | | | Oxidation products | | Alkaline impurities | | | Sum |
|---|---|---|---|---|---|---|---|---|---|
| | [Gly$^9$OH] | [Asp$^5$] | [Glu$^4$] | Sulfoxide I | Sulfoxide II | [D-Asn$^5$] | [βAsp$^5$] | Unknown 2.0 min | |
| 6.5 | 0.88 | 0.49 | 0.32 | 0.03 | 0.06 | 2.30 | 1.25 | 1.31 | 8.8 |
| 7.0 | 1.53 | 0.71 | 0.43 | 0.05 | 0.04 | 4.10 | 1.68 | 1.65 | 12.9 |

As discussed below with reference to Example 3a, the specification limit for sum of impurities (for the current PABAL® formulation) is ≤5%. As can be seen from Table 2b ("Sum"), the Samples at pH 5.2 and 5.65 (examples of the invention) are still within specification after 52 weeks (1 year) at 40° C., while all other samples are out of specification after 52 weeks (1 year) at 40° C.

The results of the pH study (FIGS. 4, 5) confirmed the observations of the antioxidant study. The formation of hydrolysis products ([Gly$^9$OH], [Asp$^5$] and [Glu$^4$]carbetocin) was effectively reduced by an increase in pH from pH 4.0 to about pH 5.65. At higher pH values (pH 6.1-7.0) the content of hydrolysis products was again increased. The effectiveness of the antioxidant at about 1 mg/ml concentration was also confirmed (in the antioxidant study the concentration of antioxidant was 5 mg/ml). However, if oxidation is limited in the drug or drug solution (e.g. if the drug or drug solution is not prone to oxidation), the amount of antioxidant may be reduced, or use of antioxidant may not be necessary. Due to the antioxidant, the oxidation of carbetocin was negligible, regardless of pH. The upper pH limit of an optimised formulation was instead limited by the alkaline degradation of carbetocin. The main impurity by alkaline degradation was [D-Asn$^5$]carbetocin, which was rapidly increased at pH values above pH 6.1. The formation of two other minor impurities at high pH was also observed, [βAsp$^5$]carbetocin and one unknown impurity eluting early in the chromatogram (tR: 2.0 min).

The U-shape of the pH vs. sum of degradation products curve illustrates the stability plateau of carbetocin at pH 5.0-6.0. At pH 5.2 the sum of degradation products was found to be only 16% of the sum of degradation products at pH 4.0 (current formulation). The optimal pH was found to be somewhere between pH 5.1 to 6, for example between around pH 5.2 and 5.65.

Examples 1 and 2 give a very strong indication that formulations of the invention are room temperature stable for up to two years.

Example 3

Formulation Study of Isotonicity Agents, NaCl Vs. Mannitol, at 30° C., 40° C.

4.22 grams of citric acid monohydrate (Merck, pro analysi) was dissolved in 2000 ml of milliQ water (20 mM). This solution was divided into ten 200 ml aliquots. 1.8 g of sodium chloride (Merck, pro analysi) was added to five of the flasks, to the other five flasks 10 g of mannitol (VWR, Ph Eur) was added. According to an experimental design, 0.2, 0.6 or 1.0 g of L-methionine (Sigma, non-animal source) was added and the pH was adjusted with 1% NaOH (Merck, pro analysi) to pH 5.2, 5.65 or 6.1, see Table 3a and 3b. 2 mg of Carbetocin (Polypeptide Laboratories,) was transferred to twelve 20 ml volumetric flasks and the substance was dissolved in each buffer (0.1 mg/ml carbetocin). The samples containing 3 mg/ml methionine were prepared in duplicate, see Table 3a and 3b.

Two mL of each solution was transferred to LC-vials and placed in a 30° C./75% RH cabinet. The remaining solutions were transferred to 25 ml blue cap flasks and placed in a 40° C./75% R.H. cabinet. The level of impurities after 25 weeks in 30° C./75% R.H are shown in the following Tables 3a and 3b.

TABLE 3a

| Formulation | Gly$^9$OH | Asp$^5$ | Glu$^4$ | Sulfoxide I | Sulfoxide II | Unknown 2 min | βAsp$^5$ | D-Asn$^5$ | D-Cys$^6$ | Sum** |
|---|---|---|---|---|---|---|---|---|---|---|
| Mannitol, pH 5.2, 1 mg/mL methionine | 0.18 | 0.04 | 0.18 | 0.04 | 0.03 | N.D. | N.D. | N.D. | 0.09 | 0.80 |
| Mannitol, pH 6.1, 1 mg/mL methionine | 0.07 | 0.03 | 0.07 | 0.03 | N.D. | 0.17 | 0.15 | 0.01 | 0.12 | 0.95 |
| Mannitol, pH 5.65, 3 mg/mL methionine, sample 1 | 0.10 | 0.03 | 0.08 | 0.04 | 0.05 | 0.09 | 0.07 | 0.05 | 0.12 | 0.78 |
| Mannitol, pH 5.65, 3 mg/mL methionine, sample 2 | 0.09 | 0.02 | 0.11 | 0.03 | N.D. | 0.08 | 0.04 | N.D. | 0.11 | 0.63 |
| Mannitol, pH 5.2, 5 mg/mL methionine | 0.17 | 0.03 | 0.20 | 0.02 | N.D. | N.D. | 0.04 | N.D. | 0.11 | 0.75 |
| Mannitol, pH 6.1, 5 mg/mL methionine | 0.10 | 0.05 | 0.05 | 0.04 | N.D. | 0.23 | 0.18 | 0.11 | 0.12 | 1.11 |

TABLE 3a-continued

| Formulation | Gly[9]OH | Asp[5] | Glu[4] | Sulfoxide I | Sulfoxide II | Unknown 2 min | βAsp[5] | D-Asn[5] | D-Cys[6] | Sum** |
|---|---|---|---|---|---|---|---|---|---|---|
| Years to OOS* for 3 mg/mL, pH 5.65 sample 2. | 8 | 12 | 7 | "infinity" | "infinity" | 6 | 12 | "infinity" | N/A | 4.2 |

*Out of specification
**of degradation products

TABLE 3b (NaCl)

| Formulation | Gly[9]OH | Asp[5] | Glu[4] | Sulfoxide I | Sulfoxide II | Unknown 2 min | Beta Asp[5] | D-Asn[5] | D-Cys[8] | Sum** |
|---|---|---|---|---|---|---|---|---|---|---|
| NaCl, pH 5.2, 1 mg/mL methionine | 0.21 | 0.06 | 0.15 | 0.02 | 0.03 | ND | 0.02 | | 0.12 | 0.82 |
| NaCl, pH 6.1, 1 mg/mL methionine | 0.08 | 0.05 | 0.04 | 0.04 | 0.04 | 0.2 | 0.12 | 0.12 | 0.11 | 0.99 |
| NaCl, pH 5.65, 3 mg/mL methionine sample 1 | 0.09 | 0.03 | 0.07 | 0.01 | ND | 0.12 | 0.04 | 0.05 | 0.11 | 0.74 |
| NaCl, pH 5.65, 3 mg/mL methionine sample 2 | 0.09 | 0.04 | 0.08 | 0.02 | 0.03 | 0.10 | 0.05 | 0.14 | 0.11 | 0.78 |
| NaCl, pH 5.2, 6 mg/mL methionine | 0.17 | 0.04 | 0.15 | 0.02 | 0.04 | ND | 0.05 | | 0.14 | 0.86 |
| NaCl, pH 6.1, 5 mg/mL methionine | 0.09 | 0.04 | 0.06 | 0.03 | ND | 0.23 | 0.17 | 0.14 | 0.11 | 1.11 |

**of degradation products

Tables 3a and Tables 3b show that there is very little degradation in all samples. This level of degradation corresponds to that seen after 6 weeks at 40° C.

The results indicate that the best samples are likely to be stable for 5 years at 30° C. As seen in Table 3a, rows 5 and 8, results for the methionine 3 mg/mL, pH 5.65 sample 2 indicate that this sample would remain in specification for more than 4 years at 30° C. and 75% RH. This is based, as is well known in the art, on a linear extrapolation of the increase in impurity over time to determine when the amount of impurity would be sufficiently high for the formulation to be "out of specification" (OOS). It was also found that the optimum pH at 30° C. is higher than at 40° C. (results not shown). The differences are small but pH 5.65 is slightly superior to pH 5.2 at 30° C. (vice versa at 40° C.). These results indicate there is a good margin for obtaining a climate zone III/IV stable formulation.

The applicants found that increase in methionine leads to more degradation, mainly by increase of [BetaAsp5]carbetocin. A concentration of about 1 mg/ml appears to be sufficient to provide effective stabilisation without significant degradation.

Experiment 3a

The Stability of Carbetocin at Different pH and Using Different Antioxidants

This study was designed to give a broader picture of the stability of carbetocin at different pH and using different antioxidants.

1.2 grams of succinic acid (Sigma-Aldrich, ≥99%) was dissolved in 1000 ml of milliQ water (10 mM). This solution was adjusted, in aliquots, with diluted NaOH (Ph. Eur., Merck) to pH 4.0, 4.5, 5.2, 5.65, 6.1, 6.5 and 7.0. 55 mg of carbetocin (Polypeptide Laboratories, Strasbourg) was dissolved in 50 ml of milliQ water (1.1 mg/ml). 1.0 ml of the carbetocin solution (1.1 mg/ml) was mixed with 10 ml of each buffer (0.1 mg/ml carbetocin). 0.55 g of mannitol (5%) was added to each solution and dissolved. The solutions were transferred to 15 ml glass vials with screw lid and placed in the 40° C./75% R.H. cabinet.

The same procedure was repeated; with the exception that 1.0 g of L-methionine (Sigma, non-animal source) was added to the 1000 ml of milliQ water, giving duplicate samples containing 1 mg/ml methionine at all pH-levels. The solutions were transferred to 15 ml glass vials with screw lid and placed in the 40° C./75% R.H. cabinet.

The buffers at pH 5.65, 6.1 and 6.5 were also divided into aliquots to which EDTA disodium, dihydrate (Fluke) was added. These samples were stored at 40° C./75% for 12 months before analysis.

Figure 7:
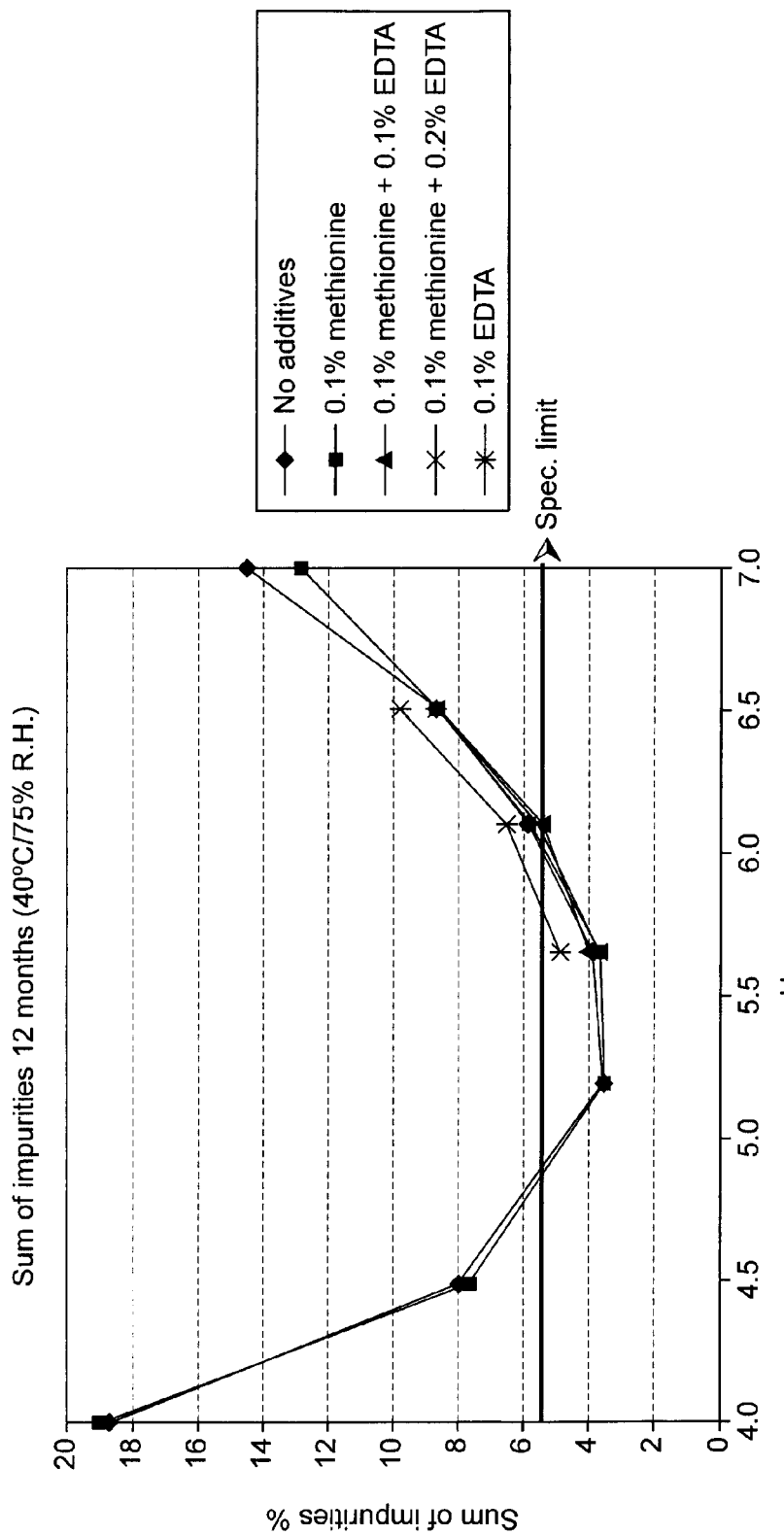
FIG. 7 shows the sum of impurities of various carbetocin formulations after 12 months at 40° C. and 75% relative humidity (R.H.), as described in Experiment 3A.

The sum of impurities after 12 months at 40° C./75% R.H are shown in FIG. 7. The Figure also shows the "spec limit", above which the sum of impurities is such that the formulation is out of specification.

All formulations at pH 5.2 and pH 5.65 were within specification after 12 months at 40° C./75% R.H.

The positive effect of methionine was visible also in this study. All samples containing methionine showed very low amounts of oxidation products, regardless of composition and pH. This points to inclusion of methionine in a robust formulation, where (for example) metal ion content of the active ingredient carbetocin, which can vary with production batch and which, if high, may lead to increased oxidation, will not be a controlled parameter.

The most stable formulation was the formulation at pH 5.2 containing 1 mg/ml of methionine (results not shown). The parameter that was closest to the specification limit after 12 months at 40° C./75% R.H. was the sum of impurities (FIG. 7). The specification limit for sum of impurities (for the current PABAL® formulation) is ≤5% (i.e. 5.5%). It can be assumed that the degradation is linear over time, and it can therefore be calculated that the formulation at pH 5.2 containing 1 mg/ml of methionine would be out-of-specification after approximately 80 weeks at 40° C./75% R.H, based on the specification for the current PABAL® formulation.

A commonly used guide, supported by the Arrhenius equation, is that the rate of most chemical reactions doubles for every 10° C. increase of temperature. If we apply this relationship to the formulation at pH 5.2 containing 1 mg/ml of methionine, the estimated shelf-life of a new formulation will be 160 weeks at 30° C., i.e. slightly more than 3 years, again based on the specification for the current PABAL® formulation. This is likely to be an underestimation, since the reported "sum of impurities" in this experiment included every peak on the baseline, including synthesis related impurities and peaks below the reporting limit (<0.05%). The synthesis related impurities consist mainly of [DCys$^6$] and [desGln$^4$]carbetocin, which do not increase during storage. The substance batch contained 0.9% impurities according to the supplier. Thus, it is likely that a shelf-life of more than 3 years at 30° C./75% R.H. would be achieved for this formulation.

Example 4

Formulation in Succinate Buffer

The following preparation and decanting was performed in a pharmaceutical room under germ free conditions. 47 grams of mannitol, 1.2 grams of succinic acid buffering agent and 1.0 g of L-methionine was dissolved in about 900 ml of milliQ water (10 mM). The pH of the solution was adjusted with 5M NaOH to pH 5.4. The solution was transferred to a 1000 ml volumetric flask and diluted to volume with WFI.

50 mg of carbetocin (Polypeptide Laboratories) was transferred to a 500 ml volumetric flask and dissolved and diluted to volume with the mannitol/succinic acid/methionine buffer pH 5.4. The solution was filtered through a 0.22 μm filter and filled in glass vials with rubber stoppers (1.1 ml per vial). Each vial included an aqueous composition comprising carbetocin (0.1 mg/mL), and the pH of the composition was 5.4 (i.e. from 5.0 to 6.0). The aqueous composition also included succinate buffer (succinic acid buffering agent), methionine (anti-oxidant) and mannitol (isotonic agent). In a further Example (Example 4A, not shown) a solution was made up exactly as Example 4 and EDTA (0.1% w/v) added. The osmolality of the solutions in Example 4 and 4A was found to be 300±20 mOsmol/kg.

The formulation of Example 4 (and that of Example 4A) is suitable for injection to a patient with uterine atony.

Example 5

Formulation in Succinate Buffer

The following preparation and decanting was performed in a pharmaceutical room under germ free conditions. 1.2 grams of succinic acid buffering agent (Sigma-Aldrich, ≥99%) and 1.0 g of L-methionine (Sigma, non-animal source) were dissolved in 1000 ml of milliQ water (10 mM) to provide a succinate buffer of pH 5.4, the pH being adjusted to this value with NaOH solution.

0.55 g of mannitol (5%) was dissolved in 10 ml of succinate buffer. Methionine 0.5% (w/v) was added to the solution and dissolved. Carbetocin (Polypeptide Laboratories) was dissolved in the solution so the concentration of carbetocin was 0.1 mg/mL, and the pH adjusted to 5.4 using NaOH solution. The solution was divided into 1 mL quantities and sealed in ampoules. Each ampoule included an aqueous composition comprising carbetocin (0.1 mg/mL), and the pH of the composition was 5.4 (i.e. from 5.0 to 6.0). The aqueous composition also included succinate buffer (succinic acid buffering agent), methionine (anti-oxidant) and mannitol (isotonic agent). It will be appreciated that the composition may be made with water for injection (WFI). The formulation of Example 5 is suitable for injection to a patient with uterine atony.

Example 6

Formulation with Citrate/Phosphate Buffer

The formulation set out in the following table was made up by similar methods to those set out in Examples 4 and 5 above.

TABLE 4

| Component | Amount per mL | Function |
| --- | --- | --- |
| Carbetocin | 10 mg | Active ingredient |
| Sodium phosphate dibasic dihdrate | 3.24 mg | Buffering agent |
| Citric acid monohydrate | 1.43 mg | Buffering agent |
| NaCl | 7.5 mg | Isotonicity agent |
| HCl | q.s. adjust to pH 5.5 | pH adjustment |
| NaOH | q.s. adjust to pH 5.5 | pH adjustment |
| Water for Injection | Adjust to 1 mL | Solvent |

The composition is suitable for nasal administration.

Optionally, an antioxidant (e.g. methionine at a concentration of 1.0 mg/mL may be included in the formulation). The anti-oxidant may be any anti-oxidant commonly used in the art.

Optionally, the composition may include an enhancer. The enhancer may be any enhancer commonly used in the art, for example any enhancer approved for use as a pharmaceutical excipient. The enhancer may be, for example, methyl-β-cyclodextrin, Polysorbate 80, carboxymethylcellulose or hydroxypropylmethylcellulose.

Example 7

The Stability of FE 202767 in Citrate and Citrate-Phosphate Buffers (pH 5.0, 5.5, and 6.0) at 40° C. for a Six Month Period Materials and Methods FE 202767 (Ferring) was synthesised by the method set out in WO2009/122285. FE 202767 was dissolved at a concentration of 0.2 mg/ml in either 25 mM citrate buffer (isotonic to saline) or 25 mM citrate-phosphate buffer (isotonic with saline) at varying pH (pH 5.0, 5.5, 6.0), by methods known in the art. The solutions were incubated at 40° C. for 176 days, with samples taken at day 0, 15, 30, 84, and 176.

Samples were evaluated by HPLC to determine the amount of intact peptide remaining at the various time points, by methods well known in the art, comparing the % Area. of the intact peptide peak on the sampling day vs. % Area on Day 0.

The HPLC method used an Agilent 1200 instrument. The mobile phases where HPLC Buffers A (A=0.01% TFA in water) and B (B=0.01% TFA in [70% v/v acetonitrile and 30% v/v water]) with the gradient 15% B for 1 min, then 15 to 95% B in 30 min, then 95 to 100% B in 3 min, then 100% B for 5 min and 100% B to 15% B in 1 min at flow rate 0.3 mL/min. The Phenomenex MAX-RP C18, 2.0×150 mm, 4 μm, 80 Å column was at temperature 40 with UV detection at 210 nm. The injection volume was 10 μL.

Figure 6:
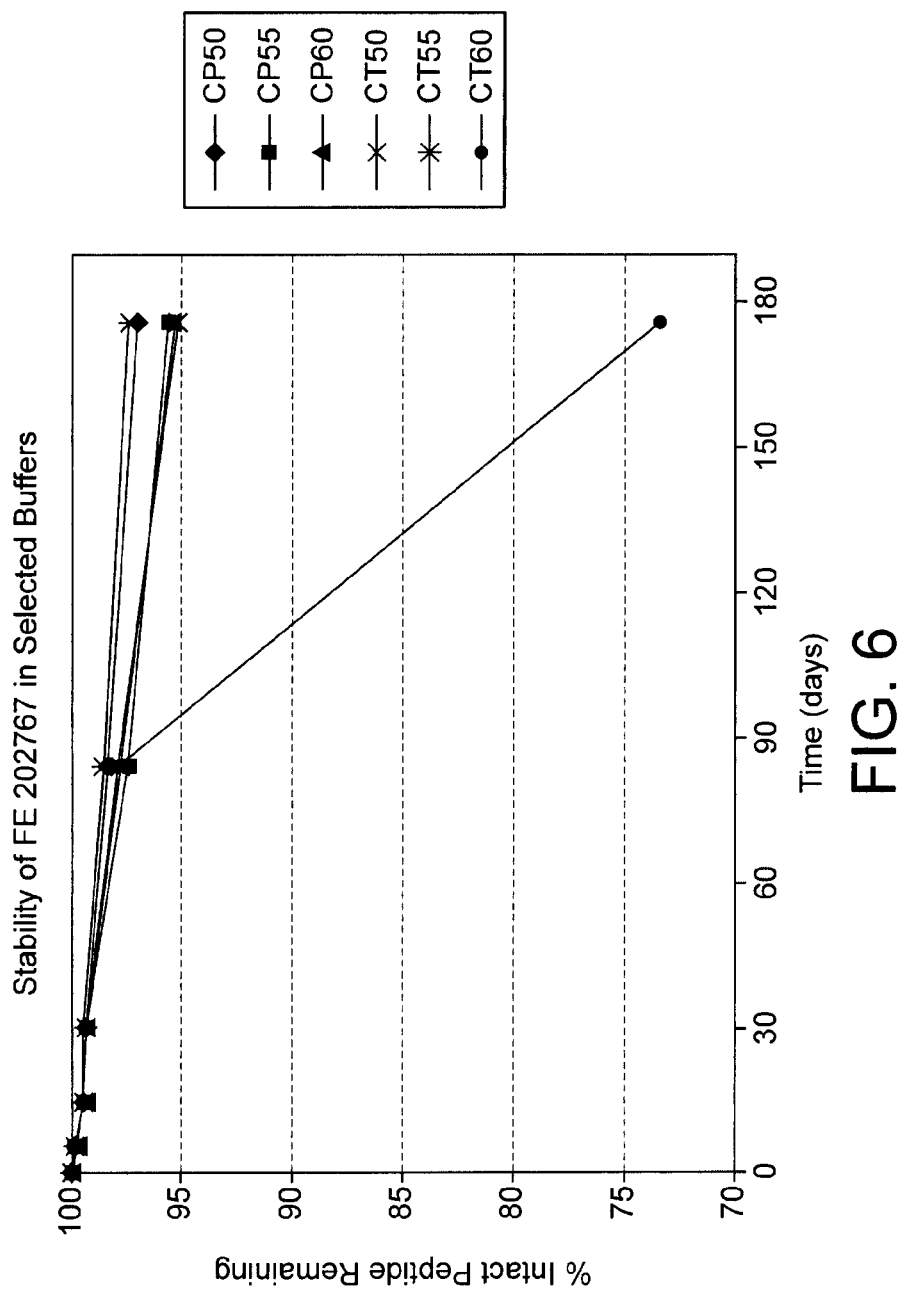
FIG. 6 shows the Stability of FE 202767 in selected buffers.

The results are shown in the following Table 5, and on the attached FIG. 6. In Table 5 and FIG. 6, CP50 is citrate phosphate buffer at pH 5.0; CP55 is citrate phosphate buffer at pH 5.5; and CP60 is citrate phosphate buffer at pH 6.0; CT50 is citrate phosphate buffer at pH 5.0; CT55 is citrate phosphate buffer at pH 5.5; and CT60 is citrate phosphate buffer at pH 6.0.

TABLE 5

| % Intact Peptide Remaining (normalised to day 0) | | | | | | |
|---|---|---|---|---|---|---|
| Day | CP50 | CP55 | CP60 | CT50 | CT55 | CT60 |
| 0 | 100.00 | 100.00 | 100.00 | 100.00 | 100.00 | 100.00 |
| 6 | 99.97 | 99.83 | 99.65 | 99.66 | 99.75 | 100.00 |
| 15 | 99.66 | 99.31 | 99.54 | 99.51 | 99.71 | 99.40 |
| 30 | 99.47 | 99.30 | 99.26 | 99.29 | n.a. | 99.30 |
| 84 | 98.38 | 97.44 | 97.78 | 98.05 | 98.61 | 97.94 |
| 176 | 96.98 | 95.60 | 95.48 | 95.19 | 97.34 | 73.36 |

Notes:
% Intact Peptide Remaining expressed relative to % Area on Day 0.
n.a. = data point excluded due to aberrant peak in HPLC chromatogram.
CP = citrate-phosphate buffer;
CT = citrate buffer.

Conclusion

FE 202767 showed good stability in citrate-phosphate buffers in the pH range tested (pH 5.0, 5.5, and 6.0), with >95% remaining after 176 days in each condition. It was also very stable (>95% remaining) in citrate buffer at pH 5.0 and 5.5; however, there was significant degradation after 176 days in pH 6.0 citrate buffer.

In general, a formulation suitable for nasal administration is expected to be of pH between 5.0 and 6.0, include the minimum number of reagents (e.g. no anti-oxidant). It is also preferred that the formulation is room temperature stable. Example 7 demonstrates that formulations along the lines above may be suitable for nasal administration, because they have appropriate pH and are room temperature stable without requirement for anti-oxidant or other additives that might adversely affect the nasal mucosa.

Example 8

The Stability of FE 202767 in Various Buffers at 40° C. for One and Three Months Materials and Methods The method was similar to Example 7. FE 202767 (Ferring) was synthesised by the method set out in WO2009/122285. The FE 202767 was dissolved at a concentration of 0.2 mg/ml in either 25 mM citrate buffer (citric acid/Na citrate), 10 mM acetate buffer (acetic acetate/Na acetate) or 10 mM succinate buffer (1 mM succinic acid+NaOH to relevant pH) at varying pH (pH 5.0, 5.2, 5.5, 5.65, 5.8, 6.0), by methods known in the art. As set out in the table below, the various samples also included isotonicity agent (NaCl, 7 mg/mL or mannitol 47 mg/mL) to achieve isotonicity. Some of the samples included oxidant (methionine 1 mg/mL, EDTA 1 mg/mL, or combination of EDTA 1 mg/mL and methionine 1 mg/mL). Each formulation (see Table below) was filled in a 10R glass vial sealed with a rubber stopper and an aluminium cap.

The solutions were incubated at 40° C. at 75% RH, with samples taken at day 30 (1 month), and day 90 (3 months).

Samples were evaluated by HPLC to determine the amount of intact peptide remaining at the various time points, by methods well known in the art, comparing the % Area of the intact peptide peak on the sampling day vs. % Area on Day 0.

The HPLC method used an Agilent 1100 instrument. The mobile phases where HPLC Buffers A (A=0.1% TFA in water) and B (B=0.1% TFA in acetonitrile) with the gradient 20 to 30% B in 40 min, then 30 to 60% B in 15 min, then 60 to 20% B in 1 min and then 20% B for 10 min at flow rate 0.5 mL/min. The Zorbax 300SB C16, 3.0×150 mm, 3.5 μm, 300 Å column was at temperature 25 with UV detection at 214 nm. The injection volume was 15 μL The results are shown in the following Table.

TABLE 6

| Sample Number | Buffer | pH | Isotonicity agent | Antioxidant | Initial peptide conc. (mg/mL) | Peptide conc. (mg/mL) at 30 days | Peptide conc. (mg/mL) at 90 days |
|---|---|---|---|---|---|---|---|
| 1 | Citrate | 6 | NaCl | No | 0.186 | 0.187 | 0.182 |
| 2 | Citrate | 5.65 | NaCl | No | 0.187 | 0.187 | 0.182 |
| 3 | Citrate | 5.8 | NaCl | No | 0.187 | 0.187 | 0.182 |
| 4 | Citrate | 5 | NaCl | Methionine | 0.187 | 0.183 | 0.162 |
| 5 | Citrate | 5.5 | NaCl | Methionine | 0.187 | 0.187 | 0.171 |
| 6 | Citrate | 6 | NaCl | Methionine | 0.186 | 0.187 | 0.181 |
| 7 | Citrate | 6 | NaCl | EDTA | 0.187 | 0.188 | 0.183 |
| 8 | Citrate | 6 | NaCl | Methionine and EDTA | 0.187 | 0.187 | 0.182 |
| 8 placebo | Citrate | 6 | NaCl | Methionine and EDTA | 0.000 | 0.000 | 0.000 |

TABLE 6-continued

| Sample Number | Buffer | pH | Isotonicity agent | Antioxidant | Initial peptide conc. (mg/mL) | Peptide conc. (mg/mL) at 30 days | Peptide conc. (mg/mL) at 90 days |
|---|---|---|---|---|---|---|---|
| 9 | Citrate | 5 | Mannitol | No | 0.187 | 0.186 | 0.173 |
| 10 | Succinate | 6 | Mannitol | No | 0.188 | 0.186 | 0.180 |
| 11 | Succinate | 5 | NaCl | No | 0.186 | 0.187 | 0.183 |
| 12 | Succinate | 5.2 | NaCl | No | 0.187 | 0.188 | 0.184 |
| 13 | Succinate | 5.65 | NaCl | No | 0.187 | 0.188 | 0.183 |
| 14 | Succinate | 6 | NaCl | No | 0.187 | 0.187 | 0.182 |
| 15 | Succinate | 5 | NaCl | Methionine | 0.187 | 0.186 | 0.182 |
| 16 | Succinate | 5.2 | NaCl | Methionine | 0.187 | 0.185 | 0.182 |
| 17 | Succinate | 5.65 | NaCl | Methionine | 0.187 | 0.186 | 0.180 |
| 18 | Succinate | 6 | NaCl | Methionine | 0.187 | 0.188 | 0.181 |
| 19 | Succinate | 5 | Mannitol | No | 0.188 | 0.186 | 0.176 |
| 20 | Succinate | 6 | Mannitol | No | 0.187 | 0.099 | 0.124 |
| 21 | Succinate | 5 | Mannitol | Methionine | 0.187 | 0.180 | 0.012 |
| 21 placebo | Succinate | 5 | Mannitol | Methionine | 0.000 | 0.000 | 0.000 |
| 22 | Succinate | 6 | Mannitol | Methionine | 0.188 | 0.023 | 0.174 |
| 23 | Acetate | 5.2 | NaCl | No | 0.186 | 0.186 | 0.183 |
| 24 | Acetate | 5.65 | NaCl | No | 0.187 | 0.187 | 0.184 |
| 24 placebo | Acetate | 5.65 | NaCl | No | 0.000 | 0.000 | 0.000 |

Conclusion

FE 202767 showed good stability in citrate and acetate buffers in the pH range tested after 30 days in each condition. It was also very stable in succinate buffer at pH 5.0 to 5.65; however, there was significant degradation after 30 days in some pH 6.0 succinate samples (sample 20, 22). The presence or absence of antioxidant seemed unimportant on a 30 day timescale.

FE 202767 also showed good stability in citrate and acetate buffers in the pH range tested after 90 days in each condition, with the best results being shown at the upper end of the pH range (e.g. between pH 5.5 and 6, see samples 1 to 6). It was also stable in succinate buffer at pH 5.0 to 5.65 after 90 days. The 30 and 90 day results for samples 21 and 22 suggest a mix up in analysis.

Again, the presence or absence of antioxidant seemed unimportant on a 90 day timescale.

The results indicate that NaCl is a better isotonicity agent than mannitol.

As indicated above, a formulation suitable for nasal administration is expected to be of pH between 5.0 and 6.0, include the minimum number of reagents (e.g. no anti-oxidant). It is also preferred that the formulation is room temperature stable. Example 8 demonstrates that formulations along the lines above may be suitable for nasal administration, because they have appropriate pH and are room temperature stable without requirement for anti-oxidant or other additives that might adversely affect the nasal mucosa.

Example 9

Formulation of FE 202767 with Citrate/Phosphate Buffer

FE 202767 (Ferring) was synthesised by the method set out in WO2009/122285. The formulation set out in the following table was made up by similar methods to those set out in Examples 4 and 5 above.

TABLE 7

| Component | Amount per mL | Function |
|---|---|---|
| carba-1-[4-FBzlGly7]dOT (FE 202767) | 0.7 mg | Active ingredient |
| Sodium phosphate dibasic dihdrate | 3.24 mg | Buffering agent |
| Citric acid monohydrate | 1.43 mg | Buffering agent |
| NaCl | 7.5 mg | Isotonicity agent |
| HCl | q.s. adjust to pH 5.5 | pH adjustment |
| NaOH | q.s. adjust to pH 5.5 | pH adjustment |
| Water for Injection | Adjust to 1 mL | Solvent |

The composition is suitable for nasal administration.

Optionally, an antioxidant (e.g. methionine at a concentration of 1.0 mg/mL may be included in the formulation).

The invention claimed is:

1. An aqueous composition comprising carbetocin or a pharmaceutically acceptable salt thereof;
wherein the composition comprises from 0.05 mg/mL to 0.1 mg/mL carbetocin or a pharmaceutically acceptable salt thereof and from about 1 mg/mL to about 5 mg/mL anti-oxidant, the pH of the composition is from 5.2 to 5.65, and after the composition is stored at 40° C. and 75% relative humidity for 12 weeks, the composition has a sum of impurities of less than 1% of the total weight of the impurities and carbetocin in the composition.

2. The composition of claim 1, wherein the pH of the composition is from 5.26 to 5.65.

3. The composition of claim 1, wherein the pH of the composition is from 5.4 to 5.65.

4. The composition of claim 1 comprising a buffering agent.

5. The composition of claim 4 wherein the buffering agent is succinic acid.

6. The composition of claim 4, further comprising an isotonicity agent.

7. The composition of claim 6, further comprising a pH adjusting agent.

8. The composition of claim 1 comprising a buffer.

9. The composition of claim 8 wherein the buffer is a succinate or citrate/phosphate buffer.

10. The composition of claim 1 wherein the anti-oxidant is methionine, EDTA, or a combination of methionine and EDTA.

11. The composition of claim 1, further comprising an isotonicity agent.

12. A kit comprising:
the composition of claim 1; and
a container for the composition, and the container optionally having separate injection means.

13. The kit of claim 12 comprising instructions for administration of the composition.

14. An aqueous composition, consisting of:
carbetocin or a pharmaceutically acceptable salt thereof;
a pharmaceutically acceptable solvent;
a buffering agent;
an anti-oxidant;
an isotonicity agent; and
a pH adjusting agent;
wherein the composition comprises from 0.05 mg/mL to 0.1 mg/mL carbetocin or a pharmaceutically acceptable salt thereof and from about 1 mg/mL to about 5 mg/mL anti-oxidant, the composition has a pH from 5.2 to 5.65, and after the composition is stored at 40° C. and 75% relative humidity for 12 weeks, the composition has a sum of impurities of less than 1% of the total weight of the impurities and carbetocin in the composition.

15. The composition of claim 14, wherein the composition consists of:
carbetocin or a pharmaceutically acceptable salt thereof in the amount of from 0.05 mg/mL to 0.1 mg/mL;
methionine in the amount of from about 1 mg/mL to about 5 mg/mL;
mannitol;
succinic acid;
sodium hydroxide; and
water.

16. The composition of claim 15, wherein the composition consists of:
carbetocin or a pharmaceutically acceptable salt thereof in the amount of from 0.05 mg/mL to 0.1 mg/mL;
methionine in the amount of from about 1 mg/mL to about 5 mg/mL;
mannitol in the amount of from about 5 mg/mL to 75 mg/mL;
succinic acid;
sodium hydroxide; and
water.

17. The composition of claim 16, wherein the composition consists of:
carbetocin or a pharmaceutically acceptable salt thereof in the amount of 0.1 mg/mL;
methionine in the amount of about 1 mg/mL;
mannitol in the amount of about 50 mg/mL;
succinic acid in the amount of about 1.2 mg/mL;
sodium hydroxide; and
water.

* * * * *

UNITED STATES PATENT AND TRADEMARK OFFICE
CERTIFICATE OF CORRECTION

PATENT NO. : 9,566,311 B2
APPLICATION NO. : 13/824132
DATED : February 14, 2017
INVENTOR(S) : Siekmann et al.

Page 1 of 1

It is certified that error appears in the above-identified patent and that said Letters Patent is hereby corrected as shown below:

On the Title Page

Item (75) Inventors, should read:
Mattias Malm, Copenhagen (DK);
Anders Nilsson, Copenhagen (DK)

Signed and Sealed this
Sixth Day of August, 2019

Andrei Iancu
*Director of the United States Patent and Trademark Office*